(12) United States Patent
Miller et al.

(10) Patent No.: US 6,898,533 B1
(45) Date of Patent: May 24, 2005

(54) METHODS FOR PREDICTING THE BIOLOGICAL, CHEMICAL, AND PHYSICAL PROPERTIES OF MOLECULES FROM THEIR SPECTRAL PROPERTIES

(75) Inventors: Dwight W. Miller, Pine Bluff, AR (US); Richard Beger, White Hall, AR (US); Jackson O. Lay, Jr., Little Rock, AR (US); Jon G. Wilkes, Little Rock, AR (US); James P. Freeman, White Hall, AR (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/629,557

(22) Filed: Jul. 31, 2000

Related U.S. Application Data

(63) Continuation-in-part of application No. 09/496,314, filed on Feb. 1, 2000, now abandoned.

(51) Int. Cl.[7] .......................... G06F 19/00; G01N 31/00
(52) U.S. Cl. .............................. 702/27; 702/28; 702/30
(58) Field of Search .............................. 702/27, 28, 30

(56) References Cited

U.S. PATENT DOCUMENTS

| | | | |
|---|---|---|---|
| 5,025,388 A | 6/1991 | Cramer, III et al. |
| 5,218,529 A | 6/1993 | Meyer et al. |
| 5,751,605 A | 5/1998 | Hurst et al. |
| 5,830,133 A | 11/1998 | Osten et al. |

FOREIGN PATENT DOCUMENTS

| | | |
|---|---|---|
| JP | 10048157 | 2/1998 |

OTHER PUBLICATIONS

Collantes, Elizabeth et al., "Use of Moment of Inertia in Comparative Molecular Field Analysis To Model Chromatographic Retention of Nonpolar Solutes," *Anal. Chem.*, 68: 2038–2043 (1996).

Tong, Weida et al., "A Comparative Molecular Field Analysis Study of N–Benzylpiperidines as Acetylcholinesterase Inhibitors," *J. Med. Chem.* 39: 380–387 (1996).

Tong, Weida et al., "Quantitative Structure—Activity Relationships (QSARs) for Estrogen Binding to the Estrogen Receptor: Predictions Across Species," *Environmental Health Perspectives*, 105: 1116–1124 (1997).

Hansch, Corwin et al., "Exploring QSAR—Fundamentals and Applications in Chemistry and Biology," *ACS Professional Reference Book*, pp. 78–81, 85, 95 (1995).

Wise, Stephen et al., "A Relationship Between Reversed–Phase C18 Liquid Chromatographic Retention and the Shape of Polycyclic Aromatic Hydrocarbons," *Journal of Chromatographic Science*, 19: 457–465 (1981).

Agin, D. et al., The Action of Anesthetics on Excitable Membranes: A Quantum–Chemical Analysis, *Proc. N.A.S.*, 53: 952–958 (1965).

Pauling, Linus et al., "The Serological Properties of Simple Substances. IX. Hapten Inhibition of Percipitation of Antisera Homologous to the $o$–, $m$–, and $p$–Azophenylarsonic Acid Groups," *Serological Properties of Simple Substances*, 67:1003–1012 (1945).

Nishikawa, Junko et al., "3–Substituent Effect an 3–Mehtylene Substituent Effect on the Structure–Reactivity Relationship of $7_\beta$–(Acylamino)–3–cephem–4–carboxylic Acid Derivatives Studied by Carbon–13 and IR Spectroscopies," *J. Med. Chem.*, 27: 1657–1663 (1984).

Ijzerman, Adriann et al., "Quantitative Evaluation of the $\beta_2$–Adrenoceptor Intrinsic Activity of N–tert–Butylphenylethanolamines," *J. Med. Chem.*, 29: 549–554 (1986).

Bursi, Roberta et al., "Comparative Spectra Analysis (CoSA): Spectra as Three–Dimensional Molecular Descriptors for the Prediction of Biological Activities," *J. Chem. Inf. Comput. Sci.*, 39: 861–867 (1999).

Andersson et al., "Ultraviolet Absorption Spectra of all 209 Polychlorinated Biphenyls Evaluated by Principal Component Analysis," *Fresenius J. Anal. Chem.*, 357: 1088–1092 (1997).

Andersson et al., "Ultraviolet Absorption Characteristics and Calculated Semi–Empirical Parameters as Chemical Descriptors in Multivariate Modeling of Polychlorinated Biphenyls," *Journal of Chemometrics*, 10:171–185 (1996).

Andersson et al., "Multivariate Modeling of Polychlorinated Biphenyl–Induced Cypia Activity in Hepatocytes from Three Different Species: Ranking Scales and Species Differences," *Environmental Toxicology and Chemistry*, 19:1454–1463 (2000).

*Primary Examiner*—Marianne P. Allen
(74) *Attorney, Agent, or Firm*—Klarquist Sparkman, LLP

(57) ABSTRACT

Methods are disclosed for establishing a quantitative relationship between spectral properties of molecules and a biological, chemical, or physical endpoint of the molecules. Spectral data including data from nuclear magnetic resonance, mass spectrometric, infrared, and ultraviolet-visible techniques are used along with endpoint data to train a pattern-recognition program. The training yields a spectral data-activity relationship that may be used to predict the endpoint value of a molecule from its spectral data alone. Methods for rapidly screening isolated compounds or mixtures of compounds based upon their spectral data are included.

74 Claims, 18 Drawing Sheets

SDBS–Mass   FIG. 2(b)

MS-NW-6834     SDBS NO. - 1716
4, 4' - ISOPROPYLIDENEDIPHENOL
$C_{15}H_{16}O_2$     /Mass of molecular ion:    228:

| m/z | ratio |
|---|---|
| 27.0 | 1 |
| 39.0 | 4 |
| 41.0 | 3 |
| 51.0 | 2 |
| 55.0 | 2 |
| 63.0 | 2 |
| 65.0 | 5 |
| 66.0 | 1 |
| 76.0 | 1 |
| 77.0 | 3 |
| 79.0 | 1 |
| 89.0 | 1 |
| 90.0 | 1 |
| 91.0 | 9 |
| 92.0 | 1 |
| 94.0 | 2 |
| 95.0 | 1 |
| 99.0 | 4 |
| 105.0 | 1 |
| 106.5 | 2 |
| 107.0 | 4 |
| 114.0 | 1 |
| 115.0 | 1 |
| 119.0 | 19 |
| 120.0 | 2 |
| 134.0 | 1 |
| 135.0 | 4 |
| 152.0 | 1 |
| 165.0 | 2 |
| 169.0 | 1 |
| 181.0 | 1 |
| 183.0 | 1 |
| 195.0 | 1 |
| 197.0 | 1 |
| 198.0 | 1 |
| 212.0 | 1 |
| 213.0 | 100 |
| 214.0 | 15 |
| 215.0 | 1 |
| 229.0 | 35 |
| 239.0 | 5 |

| Bin Number | Spectral Intensity | Bin Number | Spectral Intensity | Bin Number | Spectral Intensity |
|---|---|---|---|---|---|
| 51 | 2 | 183 | 1 | 1025 | 62 |
| 55 | 2 | 195 | 1 | 1026 | 42 |
| 63 | 2 | 197 | 1 | 1027 | 49 |
| 65 | 5 | 198 | 1 | 1032 | 62 |
| 66 | 1 | 212 | 1 | 1034 | 47 |
| 76 | 1 | 213 | 100 | 1041 | 66 |
| 77 | 3 | 214 | 15 | 1046 | 14 |
| 79 | 1 | 215 | 1 | 1047 | 12 |
| 89 | 1 | 228 | 35 | 1048 | 19 |
| 90 | 1 | 229 | 5 | 1053 | 20 |
| 91 | 9 | 580 | 328 | 1056 | 74 |
| 92 | 1 | 590 | 223 | 1059 | 72 |
| 94 | 2 | 664 | 977 | 1060 | 72 |
| 95 | 1 | 677 | 1000 | 1062 | 57 |
| 99 | 4 | 690 | 330 | 1069 | 62 |
| 105 | 1 | 704 | 441 | 1088 | 14 |
| 106 | 2 | 834 | 21 | 1089 | 55 |
| 107 | 4 | 864 | 74 | 1095 | 60 |
| 114 | 1 | 866 | 74 | 1097 | 77 |
| 115 | 1 | 868 | 70 | 1098 | 72 |
| 119 | 19 | 873 | 46 | 1106 | 68 |
| 120 | 2 | 874 | 46 | 1114 | 41 |
| 134 | 1 | 875 | 62 | 1115 | 34 |
| 135 | 4 | 877 | 72 | | |
| 152 | 1 | 883 | 77 | | |
| 165 | 2 | 1009 | 39 | | |
| 169 | 1 | 1011 | 37 | | |
| 181 | 1 | 1019 | 4 | | |

FIG. 3 – A hypothetical set of spectrally derived molecular structure descriptors for bisphenol A.

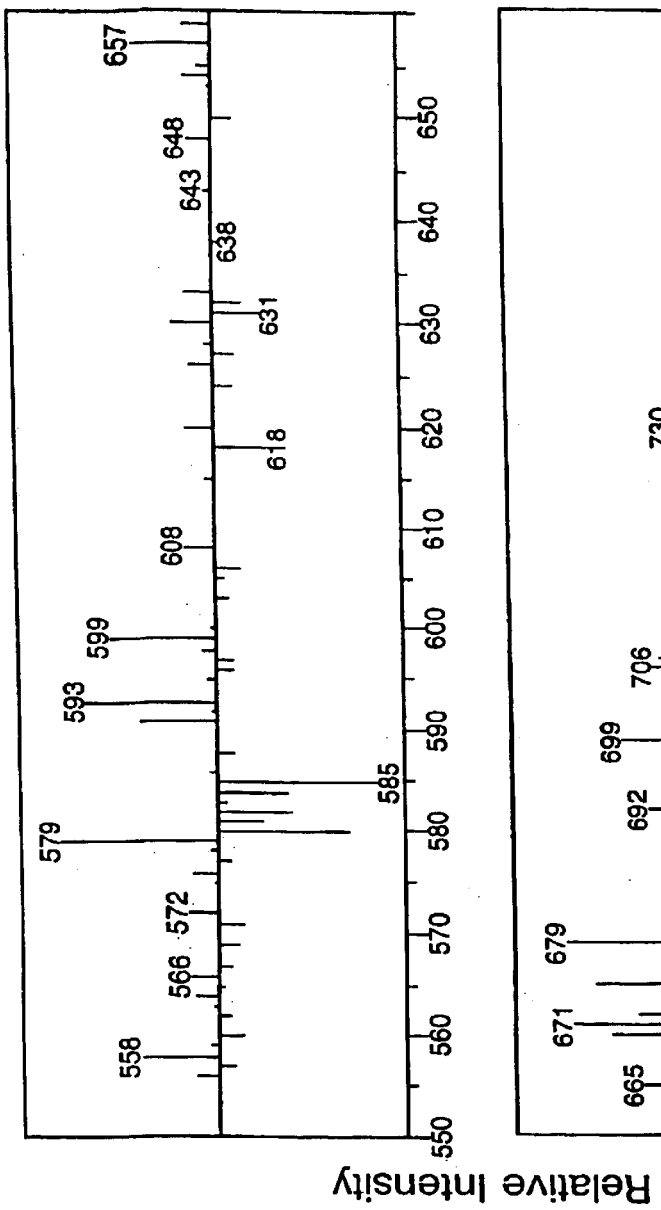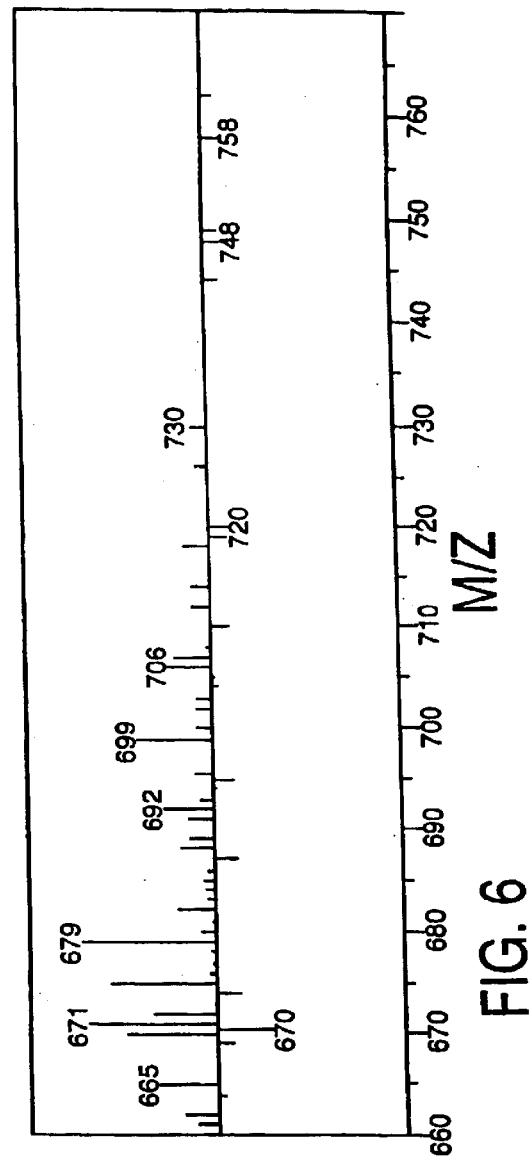
FIG. 6

US 6,898,533 B1

METHODS FOR PREDICTING THE BIOLOGICAL, CHEMICAL, AND PHYSICAL PROPERTIES OF MOLECULES FROM THEIR SPECTRAL PROPERTIES

RELATION TO PRIOR APPLICATIONS

This is a continuation-in-part of application Ser. No. 09/496,314, filed Feb. 1, 2000 now abandoned.

FIELD OF THE INVENTION

The invention relates to methods for predicting the biological, chemical, and physical properties of molecules from their spectral properties.

BACKGROUND

The number of known chemical compounds is vast, and the number is increasing constantly because methods for isolating and synthesizing molecules continue to improve. For instance, chemists are now able to employ the techniques of combinatorial chemistry to synthesize thousands of different chemical compounds at one time using a mixture of only a few interchangeable chemical building blocks. Furthermore, chemists are now able to use combinatorial computer models to generate large numbers of chemical structures that may in theory be synthesized.

While there are many chemical compounds, only a relative few of those compounds may exhibit a particular desirable property, such as pharmaceutical activity. Random testing of known compounds to find those that show pharmaceutical activity is very expensive and time-consuming. Similarly, there is a need to screen compounds for toxicity, so that rational decisions can be made regarding the use and regulation of compounds that have toxic potential. At present, only a fraction of known compounds have been thoroughly tested for their toxicological and potential therapeutic properties. To address this problem, scientists have developed methods which attempt to predict which compounds are likely to exhibit a particular property.

Methods for predicting the properties of chemical compounds are generally based upon the related observations that the structure of a compound is related to its biological, chemical, and physical properties, and that compounds of similar structure exhibit similar properties. These observations have been used to search for new compounds exhibiting a particular property. For instance, a benzene ring is present in both acetaminophen and salicylamide, both of which are analgesics. Although incorporating a benzene ring into a new molecule increases the likelihood that it too will exhibit analgesic activity, this deduction only narrows the compounds to be tested. This approach is still basically one of trial and error, because many compounds with a benzene ring are not analgesics. Moreover, analgesics without a benzene ring will be missed in the search.

Quantitative structure-property relationships and quantitative structure-activity relationships (collectively QSAR) are attempts to quantify the observed relationships between the structure of chemical compounds and the extent to which those compounds exhibit certain properties. For instance, a QSAR might attempt to quantify how the analgesic activity of known analgesics that contain a benzene ring (such as acetaminophen and salicyamide) depends upon the number and identity of substituents on their benzene rings. Once established, such a QSAR could be used to predict the analgesic activity of other compounds that contain benzene rings, and identify those compounds that warrant further investigation as analgesics based on their predicted analgesic activity.

In the terminology associated with the QSAR method, the property for which a prediction is sought, such as analgesic activity, is termed the "endpoint." In general the endpoint may be any measurable biological, chemical or physical property.

To establish a QSAR, endpoint values are obtained for a set of compounds and a correlation is then sought between the endpoint values and some measure(s) of structure available for each of the compounds. The measures used to describe or reflect the structure of the compounds for which a correlation is sought are termed structure descriptors. Structure descriptors may be defined directly with reference to the known structures of the compounds, or may indirectly reflect the structure through a property of the molecule that is sensitive to changes in structure. For example, an investigator might try to correlate the analgesic activity of compounds that contain a benzene ring with either a direct measure of the structure, such as the number of hydroxyl groups attached to the benzene ring, or an indirect measure of the structure of the compounds, like water solubility. If the direct measure is chosen, the attempted correlation could only include those compounds with hydroxyl groups on the benzene ring, while the indirect measure is more general and could be used to include all benzene ring containing compounds in the attempted correlation.

The endpoint data and the structure descriptor(s) for the set of compounds that are chosen to establish a QSAR are termed the training set. In general, the reliability of a QSAR increases as the number of compounds in the training set increases. If possible, the training set desirably includes compounds that exhibit a wide range of endpoint values and possess diverse structures.

If the endpoint and structure descriptor(s) are sufficiently correlated, a mathematical or graphical representation may be obtained. For example, the growth inhibition of certain gram negative bacteria by aromatic amines is correlated in a linear fashion with the logarithm of the octanol-water partition coefficient, and the correlation indicates that as the aromatic amines become more hydrophobic they are more likely to inhibit the growth of these bacteria (Hansch and Leo, *Exploring QSAR: Fundamentals and Applications in Chemistry and Biology*, American Chemical Society, 1995, p. 416).

The QSAR representation may be used to predict endpoint values for other compounds from their structure descriptor(s), and the reliability of a QSAR may be tested using a validation set of data. A validation set includes structural and endpoint data for compounds that were not part of the training set. The validation set desirably exhibits a diversity of endpoint values and structures that is commensurate with the training set. The QSAR is tested by how reliably it predicts endpoint data for the validation set compounds from the validation set structural data. For example, α-naphthylamine, an aromatic amine, is about two times less toxic than predicted by its octanol-water partition coefficient, indicating that the simple linear relationship described above is not always reliable and that some specific interaction is responsible for its behavior.

The Hammet equation is another example of a simple QSAR that relates a single structure descriptor (in this case, derived directly from the structure of the compounds) to an endpoint (in this case, the equilibrium or rate constant for a particular type of reaction). The Hammet equation is a linear equation of the form:

$$\ln K_x = \rho\sigma + \ln K_H$$

The electronic parameter ($\sigma$) is a measure of the ability of a group of atoms (typically a substituent at a particular structural position) to donate (negative value) or withdraw (positive value) electron density to or from the reaction center of the molecule to which it is attached. The slope parameter (ρ) is a measure of the sensitivity of the reaction to the withdrawal or release of electron density, and is constant for a particular type of reaction. $K_x$ and $K_H$ are, respectively, the equilibrium constant for reaction of the substituted molecule and the equilibrium constant for reaction of the unsubstituted parent molecule. The reaction rate constants, $k_x$ and $k_H$, may replace the equilibrium constants. A plot of ln $K_x$ (or ln $k_x$) versus σ is often linear and may be used, for example, to predict the equilibrium constant (or rate constant) for other structurally similar compounds from only the σ values of their substituents.

The Hammet parameter σ is an example of a structure descriptor that is derived from experimental data for compounds of known structure. As described above, σ is a measure of the electronic properties of a substituent. Specifically σ measures the ability of a substituent at a particular position to donate or withdraw electron density and may be defined according to the following equation:

$$\sigma = \log K_x - \log K_H$$

where $K_x$ and $K_H$ are, respectively, the acid ionization constants for an aromatically substituted benzoic acid derivative and for unsubstituted benzoic acid. The parameter σ for amino group substitution in a position para to the reaction center is determined, for example, from the measured acid ionization constants of p-aminobenzoic acid and benzoic acid using the above equation. Although depending on the position of substitution, electron-withdrawing substituents generally tend to stabilize the anion formed when benzoic acid ionizes, making $K_x$ larger than $K_H$ and σ positive. Conversely, electron-donating substituents tend to destabilize the anion and generally have negative σ values that are also dependent upon the position of substitution. Acid dissociation data for benzoic acid derivatives with various substituents in ortho, meta or para positions have been used to generate σ values for many substituents in these structural positions. Unfortunately, the σ values derived for substituents in this manner are typically not valid for multiply substituted molecules because σ values may not be additive.

Due to the inability of σ values to accurately reflect the cumulative electronic effect of multiple substituents, alternative structure descriptors have been investigated. For example, Ijzerman et al. derived structure descriptors from the assigned $^{13}C$ NMR shifts of the aromatic carbons in a family of N-tert-butylphenylethanolamines (Ijzerman et al., J. Med. Chem., 29: 549–554, 1986). Ijzerman et al. subtracted the value of the chemical shift for the carbon atoms in benzene (128.5 ppm) from the assigned chemical shift values for each of the carbons in the benzene ring of each of the substituted N-tert-butylphenylethanolamines to yield sets of structure descriptors for the compounds. A correlation was found between certain linear combinations of these structure descriptors and the $\beta_2$-andrenoreceptor intrinsic activity of the substituted N-tert-butylphenylethanolamines. Since these structure descriptors are defined in a manner similar to the Hammet σ parameter, they necessarily rely upon knowledge of structure beforehand. Also, the scope of usefulness for this type of structure descriptor is limited to the compounds containing a benzene ring. Furthermore, these structure descriptors ignore the aliphatic carbon atoms of the molecules, and their contribution to the intrinsic activity (a valid assumption only when comparing the intrinsic activities of compounds that differ minimally in structure). Additionally, the correlations of Ijzerman et al. have been questioned because the structure descriptors they derived from the chemical shifts of the aromatic carbons in these compounds are themselves highly correlated, and their use leads to the unrealistic result that substitution at one ortho position of the benzene ring affects intrinsic activity in a manner opposite to substitution at the other ortho position (see, Cramer et al., Quant. Struct.-Act. Relat., 7: 18–25, 1988).

A similar attempt to utilize spectroscopically derived parameters as structure descriptors was made by Nishikawa and Tori (Nishikawa and Tori, J. Med. Chem., 27: 1657–1663, 1984). The reactivity of the β-lactam ring of 3-substituted and 3-methylene substituted cephalosporins toward alkaline hydrolysis showed a correlation with changes in the $^{13}C$ NMR chemical shift of selected carbon atoms, and with changes in the infrared (IR) stretching frequency observed for the β-lactam carbon-oxygen bond. Selection of these measures was guided by knowledge of the structure of these compounds, and the role β-lactam reactivity plays in their antibiotic activity. Like the method of Ijzerman et al., the method of Nishikawa defines its structure descriptors in terms based upon a reference compound of known structure and utilizes spectral features assigned to particular atoms of known structures. Furthermore, the method, through its definition of the structure descriptors, is similarly restricted to narrow classes of compounds that differ only by simple substitutions.

Structure descriptors may be obtained theoretically or experimentally. Dipole moments and lowest unoccupied molecular orbital (LUMO) energies are examples of structure descriptors that may be obtained from theoretical quantum mechanical calculations on known structures. Experimental data correlated with a specific structural feature, common to a set of closely related compounds, may also be used to generate measures of structure (for example, the Hammet σ parameter). Bulk experimental measures of structure, such as partition coefficients (as a measure of polarity) and molar refractivities (as a measure of steric size) can also be utilized as structure descriptors. Structure descriptors based upon bulk physical properties have the advantage that they do not require structural knowledge beforehand, however such descriptors lack specificity. For example, compounds with vastly different biological activities may have very similar partition coefficients.

A particularly important type of biological QSAR uses, as an endpoint, the ability of one molecule to bind to another molecule. An example of such an endpoint would be the ability of a series of molecules to act as ligands for a regulatory protein, such as a hormone receptor. In recognition of the important role played by three-dimensional structure, especially for biochemical reactions where molecular recognition is an important factor, the field of 3D-QSAR has emerged. The 3D-QSAR technique is exemplified by the Comparative Molecular Field Analysis (CoMFA) method of Cramer and Wold (U.S. Pat. No. 5,025,388). The CoMFA method attempts to correlate the three-dimensional steric and electrostatic properties of a series of molecules with their relative endpoint values. The steric and electrostatic properties of a molecule are obtained from quantum mechanical or electrostatic calculations based upon known molecular structures and serve as structure descriptors. The calculations, in effect, map the electron density distribution around a molecule to create a 3-D picture of its steric and electrostatic fields (collectively, the molecular field). Those steric features (e.g., bulky substituents) and/or electrostatic properties (e.g., a strong molecular dipole) that are most important in determining endpoint values are revealed by comparing the molecular fields of the molecules in the training set to their endpoints. The advantage of calculated 3D-QSAR molecular field structure descriptors is that unlike structure descriptors referenced to a certain structural feature, molecular field structure descriptors enable the identification of structurally dissimilar molecules that have similar steric and electrostatic properties.

However, a particular problem associated with the CoMFA method and other 3D-QSAR techniques is that these methods generally require some assumptions about how molecules orient themselves relative to each other upon binding. Selecting the common alignment of a training set containing diverse structures may be problematic, leading to incorrect predictions of binding ability. Furthermore, QSAR based upon quantum mechanical or electrostatic potential calculations also suffers to some extent from the inaccuracy of the calculations themselves. These calculations are by nature approximate, and become less and less reliable as molecular size increases. In addition, the effects of solvation on the quantum mechanical properties of a molecule are often difficult to calculate and typically are ignored. Finally, these calculations are time-consuming and require knowledge of the molecular structures beforehand.

Isolation and structure elucidation of molecules is an expensive and time-consuming process that is desirably avoided, especially when screening large numbers of molecules (e.g., those generated in a combinatorial library). Furthermore, many molecular structures are proprietary, so there may be reluctance on the part of investigators to share training set structural and endpoint data with competitors in a common effort to improve the reliability of predictive QSARs.

It would be advantageous to have QSAR methods that utilize structure descriptors which may be obtained without knowledge of or disclosure of molecular structures. Such structure descriptors could be more specific than bulk physical properties, and enable the QSAR methods to differentiate dissimilar molecular structures that exhibit similar bulk physical properties. Furthermore, the structure descriptors could avoid definition with reference to a particular structural element (e.g., the Hammet c parameter), and therefore be useful for establishing QSARs for more structurally diverse sets of compounds. Additionally, such QSAR methods could eliminate the costly step of structure elucidation and obviate the need for isolation of the subject compounds.

QSAR methods that utilize structure descriptors that are inherently reflective of the steric and electrostatic properties of molecules and the effects of solvation thereon are also needed. Such methods would also desirably eliminate the necessity for assumptions regarding molecular orientation in relationship to intermolecular binding and obviate the need to rely upon approximate calculations.

SUMMARY OF THE DISCLOSURE

The present invention avoids some of the foregoing problems by providing a method for predicting a biological activity of a molecule, by obtaining spectral data (such as NMR data) for a test compound, and comparing the spectral data for a test compound to a pattern derived not exclusively from the assigned spectral data (such as NMR data) of a training set of compounds having known biological activity. Similarities between the pattern of spectral data associated with the biological activity of the training set compounds and the spectral data for the test compound are detected to determine whether the test compound is predicted to exhibit the biological activity. The spectral data of the compound for which a prediction is sought need not first be correlated with corresponding structural features. Furthermore, the pattern of spectral data associated with the biological activity may be derived without first correlating the spectral data with corresponding structural features. Training set patterns and similarities between the training set patterns and the test compound's spectral data are conveniently detected, in some embodiments, by segmenting the spectral data of the training set and test compounds into sub-spectral units (bins). These sub-spectral units, or bins, may be of a width corresponding to the digital resolution of the method used to generate the spectral data or greater.

For example, the biological activity of a test compound may be predicted by comparing the signals in bins of the training set spectral data that are found to be associated with a biological activity (such as strong estrogen receptor binding) to signals in corresponding bins of the spectral data of the test compound. Numerous signals in the test compound's spectral data that fall within bins corresponding to strong estrogen receptor binding are an indication that the test compound possesses strong estrogen receptor binding. Some of the bins of the training set spectral data may contain signals more consistently associated with strong estrogen receptor binding, in which case the presence of signals in the corresponding bins for the test compound would be more heavily weighted in assigning a predicted biological activity to the test compound. Lesser numbers of signals in the test compound's spectral data that fall within bins corresponding to strong estrogen receptor binding indicate that the test compound possess only moderate or weak estrogen receptor binding.

The spectral data of the training compounds and the test compound may be just one type of spectral data (such as NMR, for example $^{13}$C-NMR), or more than one type of spectral data (such as a composite of two or more of NMR, mass spectral, infrared, ultraviolet-visible, fluorescence, or phosphorescence data). In particular embodiments, the spectral data is a composite of two or more of nuclear magnetic resonance spectroscopic (NMR) data, mass spectroscopic (MS) data, infrared (IR) spectroscopic data, and ultraviolet-visible (UV-Vis) spectroscopic data.

In other embodiments, the spectral data of the training set compounds is segmented into sub-spectral units (bins), and scaled to normalize the importance of different signals (e.g., those from different types of spectra in a composite or those arising from signals of different inherent intensities) prior to pattern recognition. In particular embodiments, the scaling is auto-scaling. In yet other embodiments, the spectral data of the training set compounds is weighted prior to pattern recognition to emphasize those sub-spectral units (bins) that are most important for differentiating endpoint classes (such as strong versus weak estrogen receptor binding) of compounds in the training set. In more particular embodiments, the weighting is Fisher-weighting.

A pattern of spectral data associated with a biological activity can be advantageously derived from the training set spectral data using computer implemented pattern recognition techniques. Furthermore detection of similarities between the pattern derived from the training set spectral data and the spectral data exhibited by a test compound is also advantageously performed using computer implemented methods. In one such approach, the pattern of spectral data associated with a biological activity is derived for a training set of compounds by segmenting the spectral data and generating a set of canonical variate factors, one for each bin of the segmented spectral data. These canonical variate factors are used with the spectral data of a test compound to yield a prediction of the biological activity of the test compounds.

The methods of the present invention are advantageously computer implemented. In one such embodiment, the method is a computer implemented system for predicting biological activity of a test compound, in which input spectral data is received for a test compound, and for a set of training compounds having a known biological activity. The spectral pattern derived from the training set (derived, for example, using computer implemented pattern recognition programs) and the spectral pattern of the test compound are compared to determine whether the spectral patterns of the test compound match spectral patterns of the training set associated with a biological activity. The spectral data for the test compound and the spectral data for the training set may conveniently be divided into substantially identical spectral bins, so that a signal within individual corresponding spectral bins is compared between the pattern derived from the training set and the test compound.

In this computer implemented system, the spectral patterns are obtained by inputting spectral data such as one or more of nuclear magnetic resonance data, mass spectral data, infrared data, ultraviolet-visible data, fluorescence data, and phosphorescence data. In particular embodiments, the spectral data is a composite of nuclear magnetic resonance data and mass spectral data. The spectral data of the training set is converted into principal components (PCs) and canonical variates (CVs). Peaks in particular bins of the canonical variates that are associated with a biological activity (such as high affinity to a hormone receptor) are identified, and the test compound is analyzed for the presence of one or more (and ideally many) corresponding peaks in its composite spectrum.

Another aspect of the invention is a method for predicting a biological, chemical, or physical property of molecules, by providing spectral data segmented into spectral sub-units, for a plurality of training compounds; inputting the segmented spectral data and endpoint data into a pattern-recognition program; training the pattern-recognition program with the segmented spectral data and endpoint data to establish a relationship between the spectral sub-units of the segmented spectral data and the endpoint; providing segmented spectral data for a test compound that is segmented into substantially the same spectral sub-units that were used for the training set, and comparing the relationship between the spectral sub-units of the segmented spectral data and the endpoint to the spectral sub-units of the test compound's segmented data to predict the endpoint of the test compound. In this method, the structures of the training compounds and the test compound are not necessarily known beforehand. In particular embodiments of the method, the segmented spectral data of the training set is auto-scaled and Fisher-weighted before training the pattern recognition program.

The spectral data is chosen from the group consisting of nuclear magnetic resonance data, mass spectral data, infrared data, UV-Vis data, fluorescence data, phosphorescence data, and composites thereof, for example $^{13}$C NMR data, EI MS data, and composites thereof. The endpoint may be a ligand-target molecule-binding affinity, such as estrogen-receptor binding affinity. Other examples of the endpoint are a measure of biodegradability; a measure of toxicity; participation in a metabolic pathway; a partition coefficient; a reaction rate; a quantum yield, a measure of phototoxicity, an equilibrium constant; and a site of reaction on a molecular structure. In a particular embodiment, the endpoint is the octanol/water partition coefficient.

Additional non-spectral structure descriptors may be utilized along with segmented spectral data to provide an expanded set of structure descriptors useful for establishing a predictive relationship for the endpoint. Examples of non-spectral structure descriptors that do not necessarily require structural knowledge beforehand include partition coefficients, solubilities, relative acidities, relative basicities, pKa, pKb, reaction rates, and equilibrium constants. In a particular embodiment, the partition coefficient is the octanol/water partition coefficient. Calculated non-spectral descriptors are one example of descriptors requiring structural knowledge beforehand that may be utilized along with segmented spectral data in establishing a predictive relationship for an endpoint.

Another aspect of the invention is a method of using spectral data as a set of structure descriptors for a compound that does not necessarily require knowledge of the compound's structure beforehand, by providing spectral data of a training set of compounds and segmenting the spectral data into bins.

Yet another aspect of the invention is a method for establishing a relationship between spectral data and a biological, chemical, or physical property, by providing spectral data for a training set of compounds, segmenting the spectral data into bins, and detecting patterns in the bins of the spectral data that are associated with the property. The method may also include detecting corresponding patterns in spectral data of test compounds to select the test compounds having the property. Furthermore, the test compounds may be mixtures of compounds. The spectral data of the training set can be auto-scaled and weighted (for example by Fisher-weighting) to help identify data that are most strongly associated with the biological activity. Knowledge of the structural features that lead to the spectral data is not needed beforehand.

Yet another aspect of the invention is a method of determining the structural features of a plurality of compounds that contribute to determining a particular endpoint property exhibited by the compounds, by providing segmented spectral data for the plurality of compounds; providing endpoint data for the plurality of compounds; establishing a spectral data-activity relationship (SDAR) by identifying the segmented spectral features that bias toward increased endpoint values and the segmented spectral features that bias toward decreased endpoint values; and identifying the structural feature leading to the segmented spectral features that bias toward increased or decreased endpoint values for the plurality of compounds. As with the earlier described embodiments of the invention, the segmented spectral data may be a composite of several types of spectral data.

Any of the methods of the present invention can be performed without reference to a chemical structure of the test compound. Hence the spectral features of the training set and the test compound may be compared, without determining the chemical structure of the compounds of either the training set or the test compound or compounds. Any of the foregoing methods can also be incorporated into a computer readable medium, having stored thereon instructions for performing the steps of these methods.

The foregoing and other objects, features, and advantages of the invention will become more apparent from the following drawings and the detailed description of several embodiments.

BRIEF DESCRIPTION OF THE DRAWINGS

FIGS. 2(a), 2(b) and 2(c) show tables of data that correspond respectively to each of the spectra shown in FIGS. 1(a), 1(b) and 1(c).

FIG. 3 shows a hypothetical set of structure descriptors derived from the spectral data summarized in the tables of FIGS. 2(a), 2(b) and 2(c).

FIG. 6 presents the first canonical variate factor weights using $^{13}$C NMR spectral data for 30 compounds in the SDAR model. The X-axis is the bin number and the Y-axis is the factor weight relative intensity. The bins are numbered from 550 (corresponding to 0 ppm) to 770 (corresponding to 220 ppm).

DETAILED DESCRIPTION OF SEVERAL DISCLOSED EMBODIMENTS

Figure 1A:
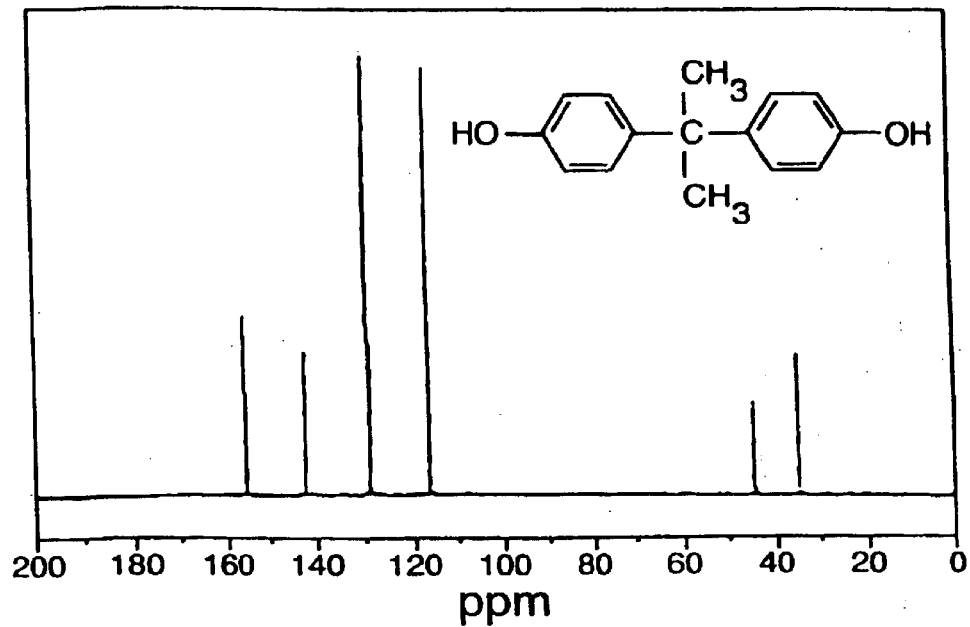
FIGS. 1(a), 1(b) and 1(c) are the $^{13}$C NMR, EI MS, and IR spectra, respectively, for bisphenol A (4,4'-isopropylidenediphenol, structure shown in FIG. 1(a)).

The illustrative embodiments that follow are best understood by first understanding terms in the art that are relevant. These terms are defined below.

Definitions and Abbreviations

LOO—leave-one-out cross validation

RBA—relative binding affinity

NMR—nuclear magnetic resonance

IR—infrared (spectroscopy)

MS—mass spectrometry

EI MS—electron impact mass spectrometry

UV-Vis—ultraviolet-visible (spectroscopy)

CODESSA—comprehensive descriptors for structural and statistical analysis

SDAR—spectral data-activity relationship

Endpoint—a particular biological, chemical, or physical property or a set of such properties for a compound that are either qualitatively or quantitatively measurable.

Structure Descriptors—any direct or indirect measure of the structure of a compound that may be obtained by theoretical or experimental means.

Training Set—endpoint data and structure descriptors (structural data) for a group of compounds used to establish a correlation between the endpoint property and the structures of the compounds.

Validation Set—endpoint data and structure descriptors (structural data) for a group of compounds used to test the reliability of the correlation between the endpoint property and the structures of the compounds.

Segmented Spectral Data—spectral data that is divided into discrete sub-spectral units (bins), each of which spans a particular spectral range. The spectral range spanned by a particular bin corresponds to a range of frequencies or a range of wavelengths for spectroscopic data and may be equal to the digital resolution of the spectral data or greater. For mass spectrometric techniques, the spectral range within each bin corresponds to a particular mass or range of masses and may be equal to the digital resolution of the spectral data or greater. The bins need not all be of equal width. The spectral data that is divided into bins may either encompass all the spectral data of a particular type that are available or cover only a portion of the spectral data of a particular type that are available. Each bin contains information derived from the spectral signals (or lack thereof) that appear within the spectral range defined by a particular bin. The structural aspect(s) of the compounds that give rise to the information falling within any particular bin need not be known.

Spectral Data-Activity Relationship (SDAR)—a correlation between endpoint data and spectral data for a group of compounds, useful for among other things for predicting the endpoint data for compounds from their spectral data.

Nuclear Magnetic Resonance (NMR)—a phenomenon exhibited by a large number of atomic nuclei in which nuclei in a magnetic field absorb energy from a radio-frequency field at certain characteristic frequencies. Particular examples of nuclei that exhibit this phenomenon include $^{13}C$, $^{1}H$ and $^{31}P$.

Mass Spectrometry (MS)—a method of chemical analysis in which the substance to be analyzed is placed in a vacuum and reduced to low pressure. The resulting vapor is exposed, for example, to a beam of electrons which causes ionization to occur, either of the molecules or their fragments. The ions thus produced are accelerated and then passed through a mass analyzer that separates the ions according to their mass.

Electron Impact Mass Spectrometry (EI MS)—a mass spectrometric technique in which the ionization of molecules and their fragments is accomplished by a beam of electrons that impacts the molecules and their fragments. Typically, as the energy of the electron beam is increased, the number of fragments produced from a molecule increases.

Infrared Spectroscopy (IR)—an analytical technique which measures a range of wavelengths (or frequencies) in the infrared region or near-infrared region of the electromagnetic spectrum that are absorbed by a specimen, which characterize its molecular constitution. Infrared absorption bands identify molecular structure components, such as aromatic, olefin, aliphatic, aldehyde, ketone, carboxylic acid, alcohol, amine, and amide groups. The frequency at which absorption occurs also reflects the frequency at which the bonds in these components stretch and and/or bend.

Ultraviolet-Visible Spectroscopy (UV-Vis)—an analytical technique which measures a range of wavelengths (or frequencies) in the ultraviolet and visible regions of the electromagnetic spectrum that are absorbed by a specimen, which characterize the electronic energy levels of its molecular constituents. UV-Vis absorption bands may be characteristic of certain molecular components, such as aromatic groups or carboxyl (CO) groups.

Fluorescence Spectroscopy—an analytical technique which measures a range of wavelengths (or frequencies) of light a molecule emits in passing from a higher to lower energy electronic state during a given time period (such as the first millisecond) after absorbing a photon of light. Fluorescence wavelengths and emission intensity reflect the redistribution of energy in the molecule after light absorption. Fluorescence excitation spectroscopy reflects the efficiency with which a molecule converts absorbed energy into fluorescent emission as a function of the wavelength of the absorbed photons.

Phosphorescence Spectroscopy—an analytical technique which measures a range of wavelengths (or frequencies) of light a molecule emits in passing from a higher to lower energy electronic state on a time scale beyond the first millisecond after absorbing a photon of light. Phosphorescence wavelengths and emission intensity also reflect the redistribution of energy in the molecule after light absorption. Phosphorescence excitation spectra reflect the efficiency with which a molecule converts absorbed energy into phosphorescent emission as a function of the wavelength of the absorbed photons.

Principal Component Analysis (PCA)—this pattern recognition technique and the related technique of partial least squares analysis reduce the structure descriptors used in SDAR to a smaller number of linear combinations of the original set of descriptors that are called principal components (PCs). The optimum number of principal components will yield the smallest standard error of prediction while capturing as much of the variance shown by the structural data as possible. (See generally, Kramer, R., *Chemometric Techniques for Quantitative Analysis*, Marcel Dekker, Inc., 1998)

Comprehensive Descriptors for Structural and Statistical Analysis (CODESSA)—a set of various structural descriptors typically utilized in three dimensional quantitative structure-activity studies that includes constitutional descriptors, topological descriptors, geometrical descriptors, electrostatic descriptors, and quantum mechanical descriptors, all of which require knowledge of structure beforehand. (See, Tong et al., *J. Med. Chem.*, 39: 380–387, 1995 and Collantes et al., *J. Anal. Chem.*, 68: 2038–2043, 1996, both of which are incorporated herein by reference)

Auto-scaling—a method whereby the quantitative spectral information contained within each particular bin is compared for all compounds in the training set to yield an average value and a standard deviation. Then, for each bin comprising the structure descriptors of a given compound, the quantitative spectral information therein is expressed as a number of standard deviations above or below the average for each bin. Autoscaling equalizes the importance of inherently weak spectral signals falling within certain bins with the importance of inherently strong spectral signals falling within certain other bins in describing a set of spectrally derived structure descriptors. It may also equalize the importance of different types of spectral data in a composite of spectral data.

Fisher-weighting—a method whereby the quantitative spectral information in bins that are important for classifying the training set compounds into different endpoint groups, such as strong and medium binders to the estrogen receptor, are enhanced. For each bin, the variance of the quantitative spectral information between the endpoint groups is divided by the variance of the quantitative spectral information within the endpoint groups. The resulting dividend becomes a weighting factor that has a magnitude larger than one when a particular bin has an important role in distinguishing the endpoint groups. Each bin is multiplied by its weighting factor to yield structure descriptors that are more sensitive to subtle but significant spectral variations.

Leave-one-out (LOO) Cross-Validation—a method whereby each compound in the training set is systematically excluded from the data set, after which its endpoint value is predicted by the spectral data-activity relationship derived from the remaining compounds (See, Cramer et al., *Quant. Struct-Act. Relat.* 7: 18–25, 1998, incorporated herein by reference). Cross-validation is useful for judging the reliability of a spectral data-activity relationship, especially where a validation set of compounds is not available.

EXAMPLES

The following examples further illustrate the QSAR methods of the present invention. The methods utilize spectral data as structure descriptors and correlate the spectral data with specific biological, chemical, or physical endpoints without the need to assign spectral features to their corresponding structural elements. In recognition of the advantages presented by using spectral data as structure descriptors, a correlation provided by the methods described herein is termed a Spectral Data Activity Relationship (SDAR).

In various embodiments, experimental and/or calculated molecular spectral data may be used as structure descriptors. If experimental spectral data is used in a particular embodiment, there is no need to actually know the molecular structures beforehand. Calculated molecular spectral data may be utilized as a surrogate for experimental data in some embodiments. In other embodiments, calculated molecular spectral data may be useful, in combination with an SDAR derived from experimental spectral data, for screening compounds that are created as part of a computer generated combinatorial library. In yet other embodiments, calculated molecular spectral data may be generated for compounds for which no experimental spectral data is available and used to establish an SDAR or to screen those compounds for a particular property.

In some embodiments, spectral data is used as a set of descriptors, for example descriptors of molecular structure. The pattern of the spectrum is determined, for example by segmenting the spectral data into portions covering particular spectral regions (e.g., ranges of frequency, wavelength, chemical shift, mass to charge ratio, and the like). The number and/or the intensity of the spectral signals within each segmented region may serve as the structure descriptors. The spectral data may be of one type or be a composite of several types, including NMR, MS, IR, UV-Vis, Fluorescence, and Phosphorescence. Spectral data of a particular type may be utilized in its entirety or in part. While spectral data are often used to elucidate the structure of the compound that yields them, the information contained in the spectra may be used in some embodiments without the need to interpret the spectra. Furthermore, the spectral data may be used in certain embodiments without the need to know the structures of the compounds beforehand. Segmented spectral data is particularly amenable to encryption for secure analysis.

Figure 1B:
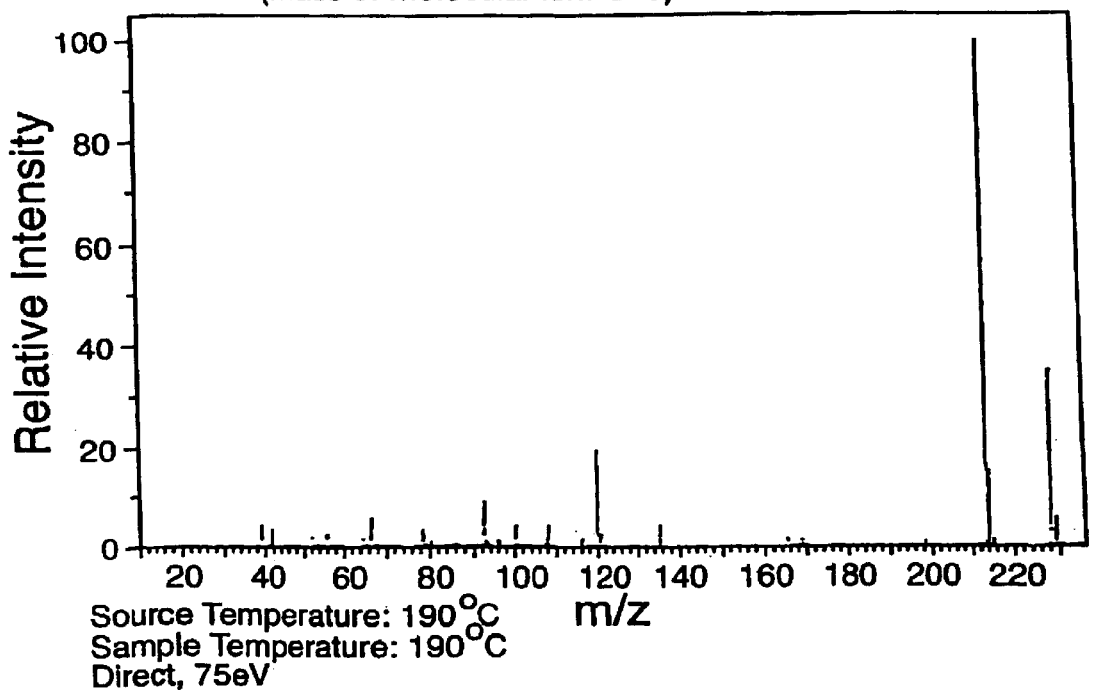
Figure 1C:
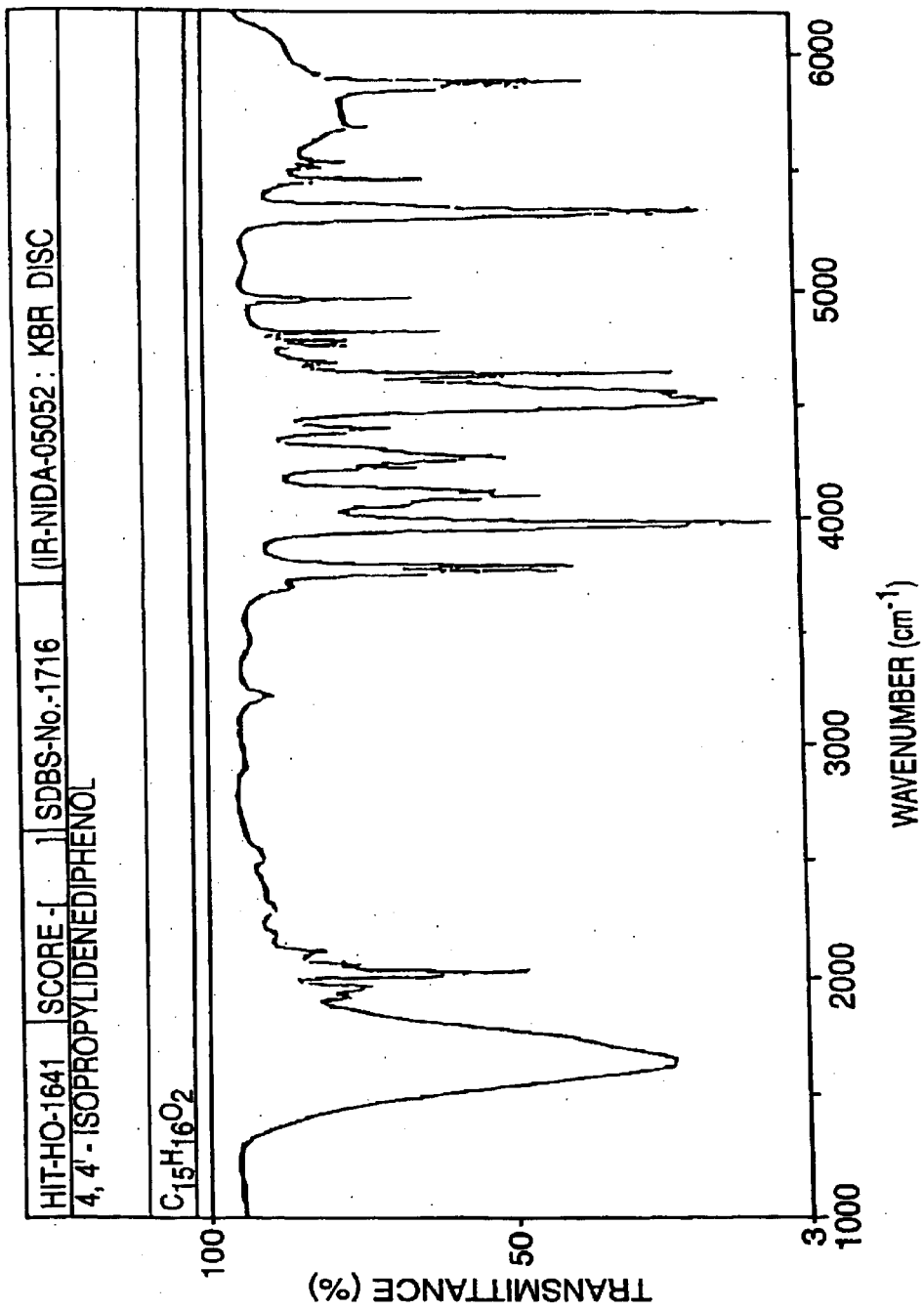

In some embodiments, $^{13}$C NMR, EI MS, and IR spectra may be combined to yield a set of structure descriptors. Examples of these types of spectra for the compound bisphenol A are shown in FIGS. 1(a), 1(b), and 1(c) respectively. Each type of spectrum contributes information regarding the structure and electronic properties of a molecule. For example, in the $^{13}$C NMR spectrum shown in FIG. 1(a), the peaks reflect the number of different types of carbon atoms and the electronic environment of each type of carbon atom in bisphenol A. Peaks exhibiting the largest δ (chemical shift) values correspond to carbon atoms of a type that are the least shielded from the applied magnetic field by the electrons of the molecule. The EI MS spectrum shown in FIG. 1(b) reveals the molecular mass (m/z=228, 228 amu) of bisphenol A and the mass of the fragments into which the molecule breaks up when the electrons impacting the molecule deliver enough energy to break bonds. For example, the most prominent peak in the mass spectrum shown in FIG. 1(b) appears at a m/z of 213. The peak at m/z=213 corresponds to the fragment formed by the loss of a methyl group ($CH_3$, m/z=15) from bisphenol A (i.e. 228−213=15). The mass spectral peaks thus reflect the fragments of structure that comprise the molecule.

The IR spectrum shown in FIG. 1(c) reveals the various types of bonds that are present in bisphenol A. For example the peak that appears at 3368 $cm^{-1}$ in the IR spectrum corresponds to the two oxygen-hydrogen bonds found in bisphenol A. While the $^{13}$C NMR, EI MS and IR spectral features have been discussed with reference to the structure of bisphenol A to illustrate the types of structural information contained in these spectra, it should be noted that in some embodiments the structure of the molecule responsible for the features need not be known and no attempt need be made to assign particular spectral features to corresponding structural features.

Figure 2A:
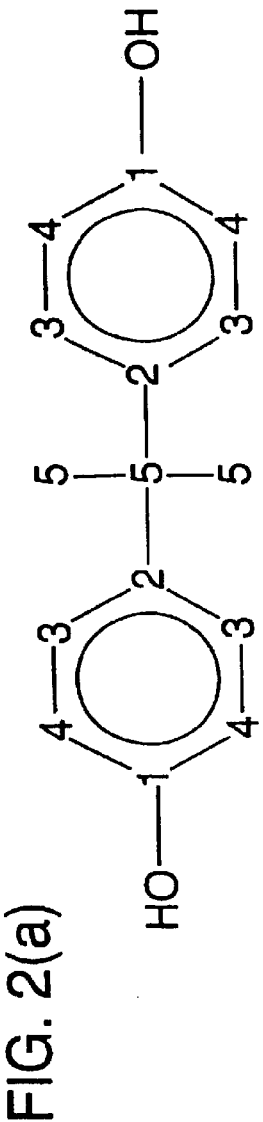
Figure 2C:
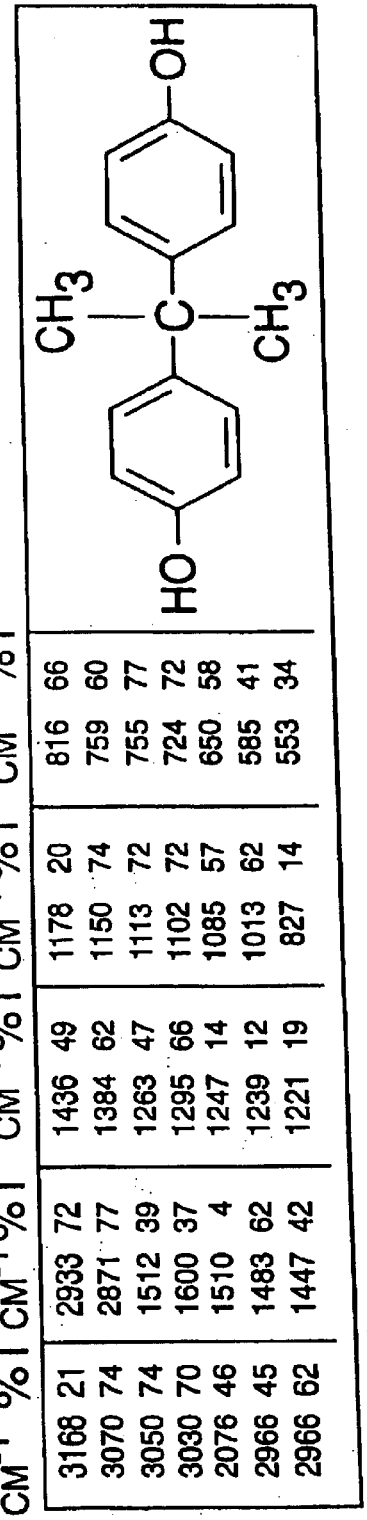

The spectral data from FIGS. 1(a), 1(b) and 1(c) are compiled in tabular form in FIGS. 2(a), 2(b) and 2(c), respectively, as tables of spectral frequencies and relative intensities. Such compilations are typical of the output of modern digital spectrometers. The data as presented in these tables may be used to construct a set of molecular structure descriptors for bisphenol A and similar sets of data may be used to generate structure descriptors for any number of compounds.

To construct the set of structure descriptors shown in FIG. 3, each type of spectrum is segmented into spectral "bins" and the information content of each bin becomes a separate structure descriptor. FIG. 3 shows a set of raw structure descriptors for bisphenol A derived, for illustrative purposes only, from the spectral data as presented in the tables of FIGS. 2(a), 2(b) and 2(c). It is possible to include more information from the spectra than considered here, such as the intensity of IR absorption at frequencies that do not correspond to a distinct peak. Each bin in this case corresponds to a particular integer m/z ratio for the EI MS data, a range of chemical shift frequencies for the $^{13}$C NMR data, and a range of wavenumber frequencies for the IR data. Moreover, each bin contains the relative intensity of the spectral feature(s) falling within a range covered by a particular bin. In this example, bins 1 to 49 were not used (because such low mass ions are common and may also result from air contamination), bins 50 to 549 correspond to m/z ratios from 50 to 549, bins 550 to 770 correspond to 1 ppm segments of the $^{13}$C NMR spectrum over the range of 0 to 221 ppm, and bins 771 to 1120 correspond to 10 $cm^{-1}$ segments of the IR spectrum over the range from 4000 $cm^{-1}$ to 500 $cm^{-1}$. Those spectral bins that do not contain spectral data are given a value of zero and are not shown in FIG. 3. Other regions of the spectra can be selected to correspond to the bins in other embodiments of the invention, which is not limited to the specific examples recited herein. In addition, the spectra can be divided into different segments, instead of the integer segments that are merely given as examples.

Tracking specific spectral data from the various spectra to the set of structure descriptors in FIG. 3 helps to illustrate how, in some embodiments, the spectral data is utilized to construct the structure descriptors. For example, the intensity of the peak at m/z=213 in the mass spectrum appears in bin number 213. The intensity of the peak appearing at 154.2 ppm in the $^{13}$C NMR spectrum is in bin number 704 because the peak falls within the range of 154 ppm to 155 ppm which corresponds to bin number 704. The peak appearing at 3368 $cm^{-1}$ in the IR spectrum falls within the frequency range 3370 $cm^{-1}$ to 3360 $cm^{-1}$ and thus the intensity of the peak appears in bin number 834 since this bin corresponds to this particular frequency range. These three entries are highlighted and shown in bold in FIG. 3.

The segmented spectral data structure descriptor set for bisphenol A shown in FIG. 3 may be altered in some embodiments to normalize the data from each type of spectrum to yield structure descriptors of similar magnitude from each type of spectral data. For example, in order to normalize the IR data and $^{13}$C NMR data to the greatest value in the MS data (100), they might be expressed as the number of peaks falling within a particular bin's range, multiplied by 100. The 21 appearing in bin 834 would thus be replaced with the value 100 as would the 411 appearing in bin 704, because in both cases only one peak appears in the spectral ranges corresponding to these bins.

In other embodiments, UV-Vis, fluorescence, and phosphorescence spectral data is segmented into bins alone or in combination with each other and with NMR, MS, and IR data.

In addition to not requiring structures beforehand, experimental spectral data as used in some embodiments offers several advantages over calculated spectral data. Most experimental spectral data reflects the quantum mechanical properties of molecules as determined by both structure and salvation. However, mass spectra do not reflect solvation. Experimental spectral data also avoids the difficulty and approximations inherent in deriving structure descriptors from quantum mechanical or electrostatic potential calculations, which are especially inaccurate when the calculations attempt to include solvation effects. Experimental spectral data may be reflective of the solution conformations that are responsible for a particular endpoint property as well as the role molecular flexibility plays in determining the endpoint property. Moreover, experimental spectral data reflect specific structural features and are therefore preferable to bulk structure descriptors such as partition coefficients that lack structural specificity. Additionally, experimental spectral data is already available for many compounds in various databases.

Figure 4:
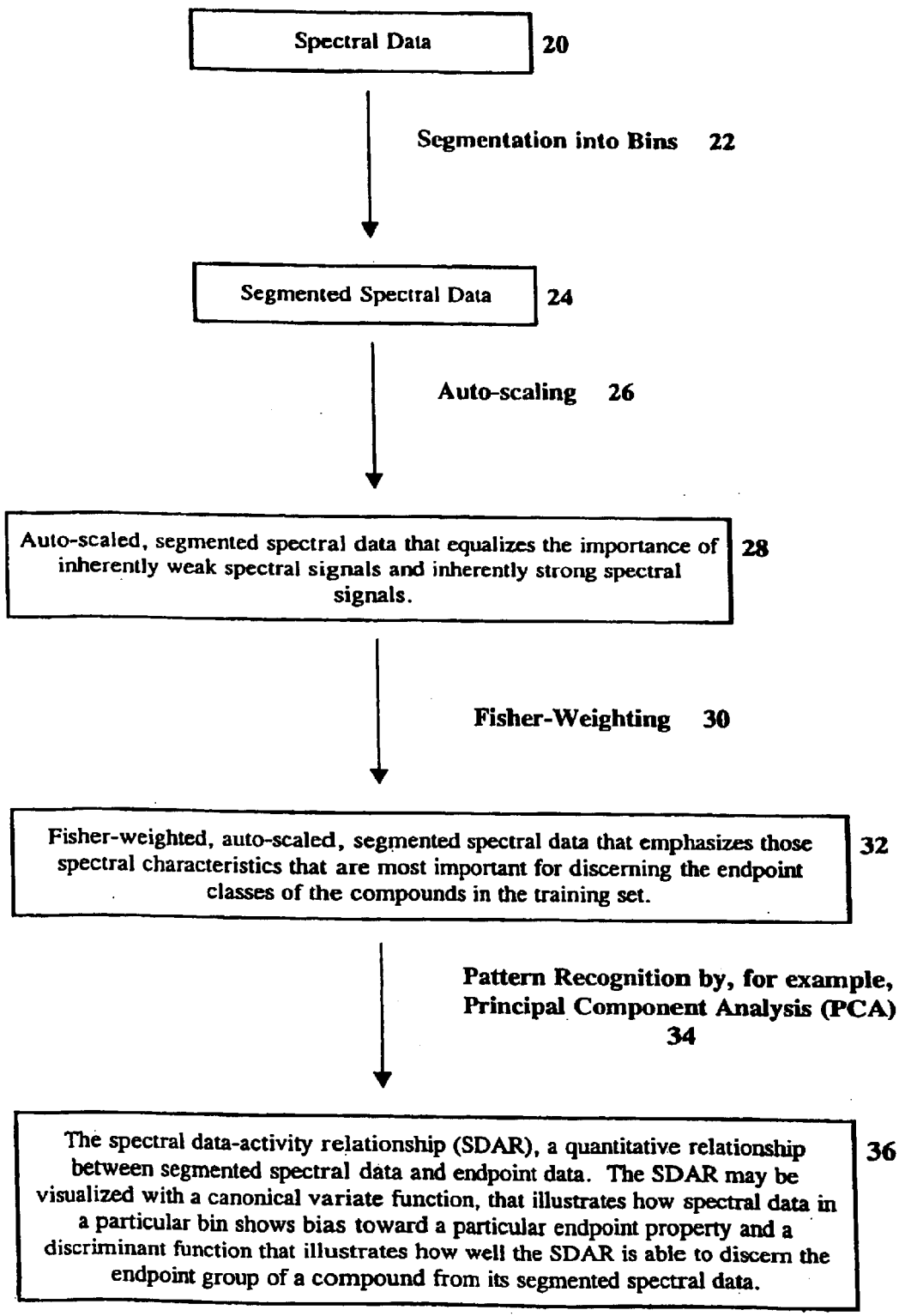
FIG. 4 shows a flowchart of a particular embodiment of the spectral data-activity relationship (SDAR) method.

In some embodiments, segmented spectral data is further pre-treated before being combined with endpoint data and subjected to statistical pattern recognition or artificial intelligence based pattern recognition to extract an SDAR. FIG. 4 summarizes, in flowchart form, a particular embodiment of the steps that may be taken to establish an SDAR from spectral data. These steps and others may be performed using a computer system.

In FIG. 4, spectral data is obtained at 20, and then the spectral data is segmented into bins at 22, which in some embodiments is carried out in a manner similar to that described above with reference to FIGS. 1, 2, and 3. The process of segmentation is repeated for the spectral data of each of the compounds in the training set. The spectral data for each of the compounds of the training set can be segmented into a matrix of bins that represent the training set. These segmented spectral data sets 24 comprise the structure descriptors for the training set compounds. Patterns in the matrix of bins can then be determined, for example by pattern recognition software.

In some embodiments, the segmented spectral data 24 is pretreated by auto-scaling 26 prior to pattern recognition, to produce auto-scaled, segmented spectral data 28. Auto-scaling is a method whereby the quantitative spectral information contained within each particular bin is averaged over all the compounds in the training set to yield an average value and a standard deviation for each bin. Then, for each bin comprising the structure descriptors of a given compound, the quantitative spectral information therein is expressed as the number of standard deviations above or below the average value for that bin. This reduces the variation in numerical magnitude between the bins in the segmented spectral data. Auto-scaling thus helps equalize the importance of inherently weak spectral signals that fall within the spectral range of certain bins with the importance of inherently strong spectral signals that fall within the spectral range of other bins.

In some embodiments, the segmented spectral data is further pre-treated by Fisher-weighting 30 the auto-scaled data 28 to improve the ability of pattern recognition algorithms to discern which bins (and the spectral information corresponding to the spectral range covered by the bin) are most important for classifying compounds into two or more endpoint classes (such as strong and weak estrogen receptor binders). An endpoint class is assigned to each compound based upon its endpoint value. For example, compounds could be classified into two endpoint classes, those compounds that have an endpoint value above a certain number and those that have an endpoint value equal to or below a certain number. For each bin of the segmented spectral data 24 the variance in value between the endpoint classes for the bin is divided by the variance in value within the endpoint classes for the bin to yield a weighting factor. The weighting factor has a magnitude larger than one when a particular bin has an important role in distinguishing the endpoint classes.

Fisher-weighting 30 quantifies the tendency for certain bins (and the spectral range corresponding to the bin) to be more helpful than others in deciding the endpoint class of a compound. For example, consider a particular bin in which the value in the bin is always large for the compounds belonging to one endpoint class (such as strong estrogen receptor binders), and always small for the compounds of a second endpoint class (such as weak estrogen receptor binders). Knowing that the spectral data for a compound yields a large value in that particular bin helps to classify the compound into the first endpoint class. If on the other hand, the value found in the bin is always large for compounds of both classes, it reveals nothing about the endpoint class of the compound to know that it has a large value in the bin. In the first case, the variance between the classes would be larger than the variance within each class and the weighting factor will be greater than one. Conversely, in the second case, the variance between the classes will be about equal to the variance within the class, making the weighting factor equal to about one. Each bin of the segmented spectral data is then multiplied by its weighting factor to yield a set of structure descriptors 32 that emphasize the bins most important for deciding the class of a compound. Such data is more easily treated by pattern-recognition analysis.

Pattern recognition 34 is used to establish an SDAR 36, by correlating the segmented (and optionally pretreated) spectral data with the endpoint data for the compounds in the training set. In particular embodiments, the compounds are classified into two or more endpoint classes (e.g. strong versus weak estrogen receptor binders) according to their relative endpoint values. The pattern recognition then determines any segmented spectral features (i.e., the bins) that are characteristic of the compounds falling into each of the classes. If Fisher-weighting is performed prior to pattern recognition, the endpoint classification scheme used for Fisher-weighting may be retained during pattern recognition. A simplified example is that a bin with a strong signal in all the compounds of the test set that have strong estrogen receptor binding would be a bin that would be considered as predictive of strong estrogen receptor binding if a test compound also exhibited a strong signal in that bin. Multiple such signals would, however, usually be taken into account by the pattern recognition software when determining spectral patterns that are associated with the endpoint.

Pattern recognition to establish an SDAR 36 may be accomplished by statistical methods or artificial intelligence methods. Underlying these methods is the idea that if a particular bin corresponds to a spectral signal exhibited by only the compounds of a particular class (e.g. strong estrogen receptor binders), the bin will bias strongly toward that class. The extent to which a particular bin biases toward a particular class depends upon whether or not compounds from all classes (e.g. strong and weak estrogen receptor binders) exhibit spectral signals corresponding to the bin. For example, if half of the compounds in one class show a signal that falls within a particular bin and slightly more than half of the compounds in another class show a signal in the same bin, the bin may only bias slightly toward the latter class. Statistical and artificial intelligence methods attempt to quantify these biases and provide a basis for classifying compounds to an endpoint class according to their segmented spectral data.

Once quantified, the relationship between the segmented spectral data and the endpoint may be visualized in various ways, depending upon the particular software package utilized for pattern recognition. One way to visualize the extent to which individual bins of segmented spectral data bias toward endpoint classes is with a canonical variate factor plot. An example of a canonical variate factor plot is shown in FIG. 6, which is discussed further with respect to Example 1. The SDAR model used to generate FIG. 6 was based upon two endpoint classes. The peaks pointing in one direction bias toward one class (strong estrogen receptor binding) and the peaks pointing in the other direction bias toward the other class (moderate estrogen receptor binding). The length of the peaks in FIG. 6 correspond to how strongly the peaks bias toward a particular endpoint class. For example, the peak appearing in bin 585 of FIG. 6 strongly biases toward the class of strong binders while the peak appearing in bin 579 of FIG. 6 biases strongly toward the other class of moderate binders.

An SDAR, once established by pattern recognition, may be used in some embodiments to quantitatively predict the endpoint value and endpoint class of any compound according to its segmented spectral data. In a particular embodiment, segmented spectral data of the type utilized to establish the SDAR is considered along with the canonical variate function to yield a prediction of endpoint class. For example, in reference to FIG. 6, a compound may be qualitatively predicted to belong to the class indicated by the upward pointing peaks if it exhibits a large number of spectral features falling into the upward biasing bins. The SDAR quantifies the prediction by considering not only the number of spectral features that fall into upward or downward biasing bins, but the strength with which each bin biases toward a particular endpoint class.

One example of a way to visualize the ability of an SDAR to correctly classify compounds into their endpoint class is with a discriminant function plot. An example of a discriminant function plot is given in FIG. 5, which is discussed in more detail with respect to Example 1. This discriminant function plot is also based upon the same two class SDAR used to generate the canonical variate function of FIG. 6. The grey and white boxes correspond to the two endpoint classes (e.g. strong and moderate estrogen receptor binding) into which the training set data was divided. The aggregation of grey boxes and the aggregation of the white boxes, as well as the separation of the two aggregates, illustrate the ability of the SDAR to discriminate between the two endpoint classes. If the SDAR had not found a correlation between the segmented spectral data and the endpoint classes, the discriminant function would have exhibited a greater mixing of the grey and white boxes.

Unlike methods using spectral data that is referenced to a parent compound's spectral data, the methods of the present invention can in certain embodiments reveal the importance of particular structural features in determining the endpoint value without requiring knowledge of the identity of those structural features beforehand. For example, if a particular bin is identified by the canonical variates as showing a bias toward strong anti-tumor activity, subsequent elucidation of the structure responsible for the signal occupying that particular bin is possible. Furthermore, spectral data as used in some embodiments is well suited for examining structure activity relationships for compounds of diverse structures where several different groupings of atoms may elicit similar quantum mechanical features that are important to a particular endpoint property.

Another benefit of using spectral data to establish an SDAR according to the methods of the present invention is the flexibility it offers. Once spectral data are gathered for a set of compounds, an SDAR may be generated with reference to a multitude of biological, chemical, or physical endpoints for which data is available. For instance, the same set of spectrally derived structure descriptors for a set of compounds may be utilized with toxicity data and antibacterial activity data for these compounds to establish two separate SDARs for the compounds, one for toxicity and the other for antibacterial activity.

Because the experimentally based SDAR method does not require input of a compound's structure, the method yields accurate results without computer modeling of a compound's steric or electrostatic properties. The method also removes the need to break the compound into secondary structural motifs or assume a particular alignment for how a set of molecules will bind to another molecule.

Methods according to the invention additionally provide rapid and inexpensive approaches to screen compounds for selected activities or properties. Screening using these methods does not require that time and effort be expended in trying to elucidate the structure of compounds beforehand, like screening using 3D-QSAR. Screening according to the methods of the present invention, by measuring a compound's spectral data and inputting it into an SDAR, is much more rapid than screening with bioassays. Furthermore, once obtained, the same spectral data for a compound may be utilized in multiple SDARs to predict various properties of the molecule. Additionally, the methods may also be used to screen mixtures or fractions of compounds for spectral features associated with a particular property, thereby obviating the need to spend time and money isolating compounds that show no promise of having the particular property. The methods may therefore be extremely useful, for example, in combination with experimentally generated combinatorial libraries of compounds.

When implemented in a real-time web-based computer environment, the methods of the present invention may provide investigators with a means for rapidly and securely estimating the molecular activities of proprietary molecular structures. Spectral data as utilized in the present invention may be generated for any number of compounds and submitted by an investigator, either directly or as a segmented set of descriptors, to a central location containing the SDAR software. The spectral data or segmented spectral data may be encrypted by the user and securely transmitted to the central location. Because of the speed at which pattern recognition software can make predictions based upon an SDAR, a submission of spectral data and retrieval of a prediction based on an SDAR can take place in real time over the worldwide web without the spectral data being stored at the central location. Alternatively, the SDAR and the pattern recognition software may be implemented on a single computer in an investigator's laboratory. In either case, there is no need to reveal the structure of a proprietary compound to obtain a prediction. The ability to provide spectral data in a pre-segmented and encrypted form that is difficult to use for structure elucidation purposes (i.e., industrial espionage) may also encourage investigators to submit their spectral and endpoint data permanently to a central location for use as part of larger training sets that may lead to more reliable SDARs.

It will be understood, however, that many variations and modifications of the methods can be made while remaining within the scope and spirit of the present invention. For example, segmentation of spectral data into bins need not occur, but is only one example of how spectral patterns may be observed and compared. Other approaches for comparing spectral patterns could also be used, for example artificial neural networks that may not require gross segmentation of the spectral data per se (image analysis).

Example 1

Use of $^{13}$C NMR and EI Mass Spectrometric Data to Produce a Predictive Model of Estrogen Receptor Binding Activity The Food Quality Protection Act, passed in 1996, mandates that the Environmental Protection Agency (EPA) develop screening and testing procedures for endocrine disrupting chemicals (EDCs). An EDC is defined as "an exogenous agent that interferes with the production, release, transport, metabolism, binding, action, or elimination of natural hormones in the body responsible for the maintenance of homeostasis and the regulation of developmental processes." Estrogenic compounds represent a significant subset of the EDCs to be tested. Many of these compounds can be screened by determining how strongly the compounds bind to estrogen receptors. Thus there is a need to develop inexpensive and rapid methods to screen thousands of potential compounds. SDAR according to the invention meets this need.

The $^{13}$C nuclear magnetic resonance (NMR) spectrum of a compound contains frequencies that correspond directly to the quantum mechanical properties of the molecule and depend largely on the electrostatic features and geometry, including the stereochemical configuration, of the molecule. Furthermore, a solution spectrum, like NMR, inherently reflects the effects of solvation on the quantum mechanical properties. Electron-impact mass spectral (EI MS) data provide a mass-size description of molecular substructures (and possibly the whole molecule) as well as information about the strength of bonds between the atoms of the molecules. The $^{13}$C NMR and EI mass spectral data thus represent sets of quantum mechanical structure descriptors that reflect the electrostatic and steric properties of a molecule. Such experimental data are readily attainable and often already available.

Two Spectral Data-Activity Relationship (SDAR) models were established, based on $^{13}$C NMR and EI MS spectra, for 30 estrogenic chemicals whose relative binding affinities (RBA) for the alpha (ERα) and beta (ERβ) estrogen receptors are available. The SDAR models classified the 30 compounds into two endpoint classes, those with strong binding affinities for the estrogen receptors and those with medium binding affinities for the estrogen receptors. The SDAR based on $^{13}$C NMR data alone yielded a leave-one-out cross-validation of 90% and the SDAR based on a composite of $^{13}$C NMR and EI MS data yielded a cross-validation of 83%. Two compounds that were classified incorrectly in both SDAR models were in a transition zone between these classifications. Both SDAR models correctly classified 25 compounds. The models provided rapid, reliable, and simple ways to predict whether a compound binds to the estrogen receptor.

Procedure

The estrogenic relative binding affinities (RBAs) of the 30 compounds were obtained from previous publications (Kuiper et al., *Endocrinology* 138:863–870, 1997; and Tong et al., *Endocrinology*, 138:4022–4025, 1997). Most of the $^{13}$C NMR spectrometric and EI mass spectrometric data were obtained from the Integrated Spectral Data Base System for Organic Compounds (AIST, Japan), the *Aldrich Library of $^{13}$C and $^1$H FT NMR Spectra* (Pouchert and Behnke, Eds., Aldrich Chemical Company, Volumes 1–3, 1993), *Spectral Data of Steroids* (Frenkel and Marsh, eds., Thermodynamics Research Center: College Station, 1994), and the NIST MS database software version 1.6. Experimental $^{13}$C NMR and EI MS data for five compounds were obtained using standard methods.

Specifically, the $^{13}$C nuclear magnetic resonance (NMR) spectral analyses of 4-hydroxy-estradiol, ICI 164,384, moxestrol, and norethynodrel were performed at 75.46 MHz on a Varian Gemini 300 MHz NMR (Varian Associates, Inc., Palo Alto, Calif.) spectrometer operating at 301 K. The subject compounds were dissolved in $CDCl_3$ or DMSO (dimethyl sulfoxide). The chemical shifts were defined by denoting the $CDCl_3$ peak at 77.0 ppm and the DMSO peak at 39.5 ppm. The spectral width was 21,008 Hz with a 2.6-second delay time between acquisitions. The acquisition time was 0.495 seconds and the number of points acquired was 20,800.

The samples were also analyzed by direct exposure probe (DEP) mass spectrometry (MS). The mass spectrometers were operated in the electron-impact (EI) mode, with 70 V electron energy. The ion source temperature was set at 150° C. Samples, in solution, were applied to the rhenium wire of the DEP and the solvent was allowed to evaporate before the analysis was begun. MS data were collected until the current of the DEP exceeded 500 mA. Norethynodrel, ICI 164,384, 4-hydroxy-tomoxifen, and 4-hydroxy-estradiol were analyzed on a Finnigan TSQ 700 mass spectrometer and moxestrol was analyzed on a Finnigan 4500 mass spectrometer (Finnigan Corp, San Jose Calif.).

The $^{13}$C NMR and EI-mass spectral data points were used as comprehensive descriptors for structural and statistical analyses (CODESSA) as in Tong et al., *J. Med. Chem.*, 39: 380–387, 1995 and Collantes et al., *J. Anal. Chem.*, 68: 2038–2043, 1996, both of which are incorporated herein by reference). Mass spectrometric data for mass-to-charge (m/z) ratios from 50 to 549 were used directly as ordered pairs of m/z and relative intensity (maximum of 100). Unassigned ID $^{13}$C NMR chemical shifts were segmented into bins over a 0 to 221 ppm range. The $^{13}$C NMR frequencies were shifted to bins 550 to 770, so bin 550 was the $^{13}$C NMR spectrum for frequencies inside 0 to 1 ppm and bin 770 was the $^{13}$C NMR spectrum for frequencies inside 220 to 221 ppm.

To save space, the $^{13}$C NMR spectra were saved as sets of ordered pairs each consisting of the respective chemical shift frequency in ppm and the respective area under the peak. The area under the peak of a specific chemical shift frequency was first normalized to an integer. A non-degenerate frequency was assigned an area of 1; a doubly degenerate frequency had an area of 2; and so forth. This was done to provide all the spectra with a similar signal-to-noise ratio and to eliminate line-width variations due to differences in NMR-instrument field strengths, shimming, temperature, pH, and solvents. The bin defined the number of significant and distinct chemical-shift peaks inside a ppm range. The optimal range in this example was found to be 1 ppm to each bin. To normalize the peak intensity of the $^{13}$C NMR spectroscopic data relative to the mass spectrometric data, the area of one $^{13}$C NMR peak was set to be 25. The number 25 was selected with the objective of scaling the maximum value for the $^{13}$C NMR data inside a bin to near 100, which is the maximum value for EI MS data. The number of bins used to input the $^{13}$C NMR spectra was studied by varying the width of the bins from 0.5 to 5.0 ppm. Again, the optimal ppm range for this study was found to be 1.0 ppm. Values were normalized to a maximum of 100 prior to pattern-recognition analysis.

The relative binding affinity (RBA) to the estrogen receptor was defined as the ratio of the molar concentration of 17-β-estradiol to the competing compound required to decrease the receptor-bound 17-β-estradiol by 50%, multiplied by 100. Thus, 17-β-estradiol has an RBA of 100 and a log (RBA) of 2.0. Strong binders to the estrogen receptor were classified as having a log (RBA) over 0.0, and medium binders to the estrogen receptor were classified as having a log (RBA) of less than or equal to 0.0. There were 17 strong binders and 13 medium binders in the training set. No weak estrogen-receptor-binding compounds (i.e., those with a log (RBA) of less than or equal to −3) were included. SDAR models that include more compounds, including weak-binding compounds, in the training set are better able to accurately predict strong estrogen receptor binding (see example 2).

The analysis of the SDAR model was performed by the leave-one-out (LOO) cross-validation procedure in which each compound was systematically excluded from the training set and its relative binding activity class predicted by the model (Cramer et al., *Quant. Struct.-Act. Relat.*, 7:18–25, 1988, incorporated by reference). The pattern-recognition software used was RESolve Version 1.2 (Colorado School of Mines, Boulder, Colo.). The $^{13}$C NMR and EI MS spectroscopic data for all 30 compounds were input as text files into a computer programmed with the software. The spectroscopic data was then auto-scaled and Fisher-weighted prior to principal component analysis (PCA). The discriminant analysis was based on canonical variate vectors. Leave-one-out (LOO) cross-validation was used to maximize the size of the training set.

Autoscaling compared the quantitative response at each mass spectral m/z bin or NMR chemical shift bin to all the other bins in the comparison set. An average value (with standard deviation) was calculated for each bin. Then, for each spectrum, the quantitative response at each bin was expressed as the number of standard deviations above or below the respective average. This data-pretreatment step equalized the weight of consistent variance of signals with inherently small magnitudes (25 units for the NMR bin 558 representing a single methyl carbon) to those signals with large magnitudes (130,000 area counts at m/z bin 91, possibly arising from a tropylium ion fragment). Autoscaling automatically compensates for gross magnitude variations. It was particularly helpful in this example in which two completely different types of analytical spectra were formed into a composite set of structure descriptors that are representative of molecular characteristics.

Fisher weighting was used to emphasize those spectral characteristics important in distinguishing defined endpoint groups. For each mass spectral m/z or NMR bin, the variance between groups was divided by the variance within groups. The resulting dividend became a weighting factor with a magnitude larger than one when the particular m/z or bin has an important role in distinguishing groups. Fisher weighting all of the raw spectra before pattern recognition increased the power of discriminant analysis to classify spectra correctly. In this example, Fisher weighting de-emphasized the relative importance of irrelevant spectral information (such as the NMR signals from carbon atoms not important to binding to the estrogen receptor).

Results

Figure 5:
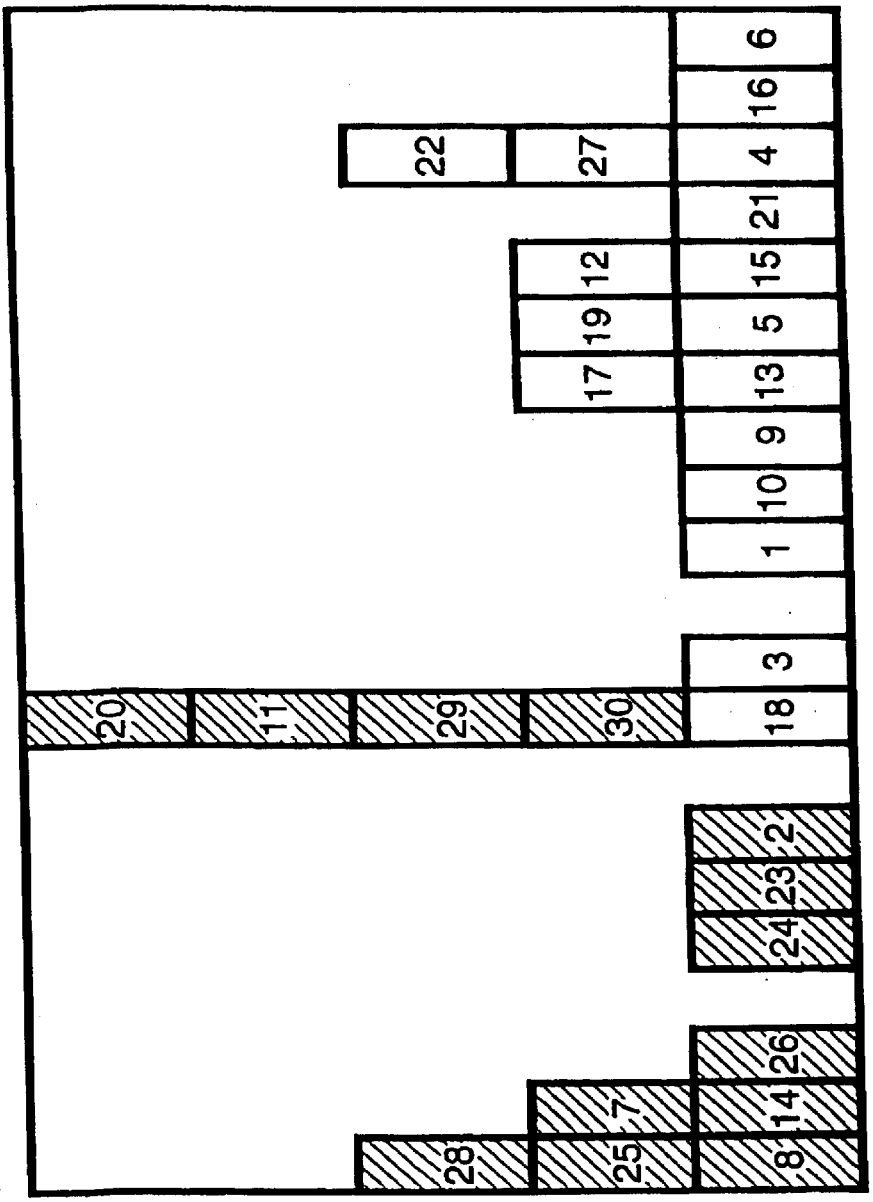
FIG. 5 shows the discriminant function using $^{13}$C Nuclear Magnetic Resonance (NMR) spectral data for 30 compounds in the Spectral Data-Activity Relationship (SDAR) model. The X-axis is the first canonical variate (discriminant function) and the Y-axis is the component frequency. The numbers in each box correspond to the numbers in Table 1 that serve to identify the compounds used in the SDAR. White boxes correspond to strong estrogen receptor binding compounds, and gray boxes correspond to medium estrogen receptor binding compounds.

Based only on $^{13}$C NMR spectroscopic data, the statistical pattern-recognition program with 8 principal components (PCs) had 81.1% of the total variance and a cross validation of 90%. The mathematical mode of significance was 91.9% at 1, with 28 degrees of freedom. The Wilks discriminant criterion was 99.99%. Table 1 lists the compound names, an identifying number for each compound that is used in FIGS. 5 and 7, the log (RBA) alpha and log (RBA) beta values, the SDAR training input endpoint class for each compound ("class input")(either S for strong binding or M for medium binding), the SDAR prediction ("class predicted NMR") from the $^{13}$C NMR data alone and the SDAR prediction ("class predicted NMR and MS") from the $^{13}$C NMR and EI MS data. FIG. 5 shows the discriminant function for SDAR derived from the $^{13}$C NMR data alone which illustrates the ability of the SDAR to discriminate between the two endpoint classes in the training set. Compounds denoted with a white background exhibit strong RBAs, and compounds with a gray background exhibit medium RBAs. FIG. 5 shows that the SDAR yielded a large separation between the 15 strong (white rectangles on right side) and the 9 medium binders (gray rectangles on the left side); 4 strong and 2 medium RBAs are in a transition zone (middle) between strong and medium RBAs. Table 1 also shows that 27 of the 30 compounds are correctly group-predicted using only, $^{13}$C NMR data. 3β-androstanediol, 2-hydroxy-estradiol and hexestrol are incorrectly predicted to have a medium RBA using 8 principal components. Only 3β-androstanediol and hexestrol are incorrectly predicted to have a medium RBA using the canonical variate function. Strong binding 3β-androstaniediol is most likely incorrectly predicted because the compound is similar to the medium REA 3α-androstanediol. Repeating the analysis using a larger training set (Example 2) eliminated even this confusion.

TABLE 1

| COMPOUND | Number | Log-(RBA) alpha | Log-(RBA) beta | Class Input | Class Predicted NMR | Class Predicted NMR + MS |
|---|---|---|---|---|---|---|
| Coumestrol | 1 | 1.97 | 2.27 | S | S | S |
| 3α-Androstanediol | 2 | −1.15 | −0.52 | M | M | S |
| 3β-Androstanediol | 3 | 0.48 | 0.85 | S | M | M |
| 4-OH-Estradiol | 4 | 1.11 | 0.85 | S | S | S |
| 17α-Estradiol | 5 | 1.76 | 1.04 | S | S | S |
| 17β-Estradiol | 6 | 2.00 | 2.00 | S | S | S |
| Bisphenol A | 7 | −1.30 | −0.48 | M | M | M |
| β-Zearanol | 8 | −1.20 | −1.15 | M | M | M |
| Clomifene | 9 | 1.40 | 1.08 | S | S | S |
| 2-OH-Estradiol | 10 | 0.85 | 1.04 | S | M | S |
| Dehydroepiandroster-one | 11 | −1.40 | −1.15 | M | M | M |
| Diethystibesterol | 12 | 2.67 | 2.47 | S | S | S |
| Dienestrol | 13 | 2.35 | 2.61 | S | S | S |
| Dihydro-testosterone | 14 | −1.30 | −0.77 | M | M | M |
| Estriol | 15 | 1.15 | 1.32 | S | S | S |
| Estrone | 16 | 1.78 | 1.57 | S | S | S |
| Genistein | 17 | 0.70 | 1.56 | S | S | S |
| Hexestrol | 18 | 2.48 | 2.37 | S | M | M |
| ICI 164,384 | 19 | 1.93 | 2.22 | S | S | S |
| Methoxychlor | 20 | −2.00 | −0.89 | M | M | M |
| Moxestrol | 21 | 1.63 | 0.70 | S | S | S |
| Nafoxidine | 22 | 1.64 | 1.20 | S | S | S |
| Nandrolone | 23 | −2.00 | −0.64 | M | M | M |
| Norethindrone | 24 | −1.15 | −2.00 | M | M | M |
| Norethynodrel | 25 | −0.16 | −0.66 | M | M | M |
| Progesterone | 26 | −3.50 | −3.50 | M | M | M |
| Tamoxifen | 27 | 0.85 | 0.78 | S | S | S |
| Testosterone | 28 | −2.10 | −2.10 | M | M | M |
| 5α-Androstanedione | 29 | <−2.0 | <−2.0 | M | M | S |
| 5β-Androstanedione | 30 | <−2.0 | <−2.0 | M | M | S |

In FIG. 6, m/z bins 550 to 770 refer to the $^{13}$C NMR data from 0 ppm to 1 ppm for bin 550 to data from 221 ppm to 222 ppm for bin 770. The canonical variate function reveals that the aliphatic $CH_2$ bins 580 to 585 (30 to 35 ppm) have a bias toward medium RBA. It also reveals that the methyl $CH_3$ bins 558 and 566 (8 and 16 ppm, respectively) have a bias toward strong RBA. Many of the benzyl bins 665 to 700 (115 to 150 ppm) have a bias towards strong RBA. Thus these methyl groups and benzyl atoms are indicated to be important for strong RBA.

Figure 7:
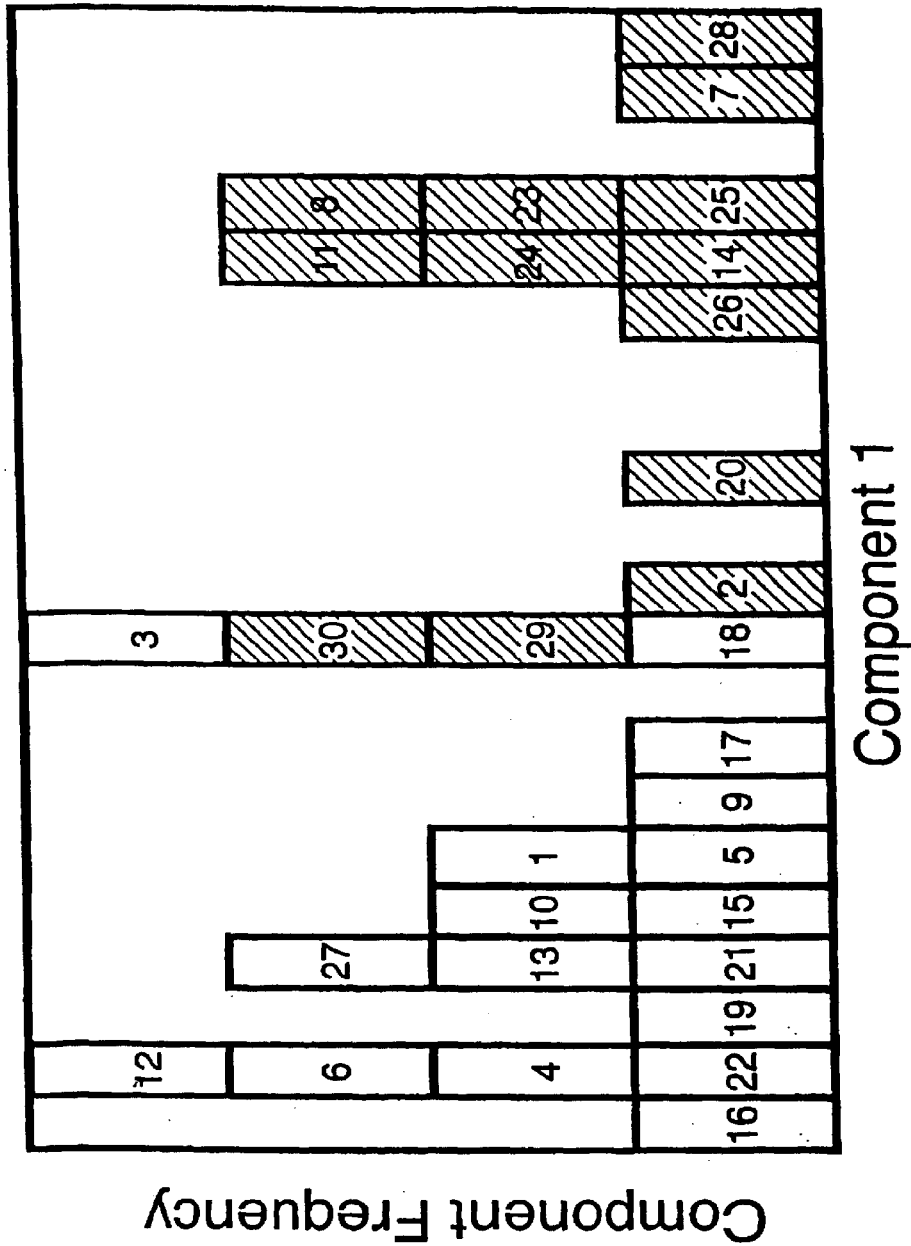
FIG. 7 shows the discriminant function using composite $^{13}$C NMR spectral data and Electron Impact (EI) mass spectral data for 30 compounds in the SDAR model. The X-axis is the first canonical variate and the Y-axis is the component frequency. The numbers in each box correspond to the numbers in Table 1 that serve to identify the compounds used in the SDAR. White boxes correspond to strong estrogen receptor binding compounds, and gray boxes correspond to medium estrogen receptor binding compounds.

Based on the composite $^{13}$C NMR and EI MS data, the statistical pattern-recognition program with 14 principal components (PCs) included 89.8% of the total variance and had a cross validation of 83.3%. The mathematical mode of significance was 97.6% at 1, with 28 degrees of freedom. The Wilks discriminant criterion was 99.89%. FIG. 7 shows the discriminant function for the composite $^{13}$C NMR and EI MS data. Compounds with a white background are strong RBAs and compounds with a gray background are medium RBAs. FIG. 7 shows a large separation between 15 strong (left) and 9 medium (right) binders. There are 2 strong and 4 medium binders in the transition zone between the strong and medium binders. Table 1 shows that 25 of the 30 compounds are correctly predicted using the composite $^{13}$C NMR and EI/MS data. Only 3β-androstanediol and hexestrol are incorrectly predicted using the canonical variate function. Again, the strong binding 3β-androstanediol is most likely predicted incorrectly because it is similar to the medium binding 3α-androstanediol.

Figure 8A:
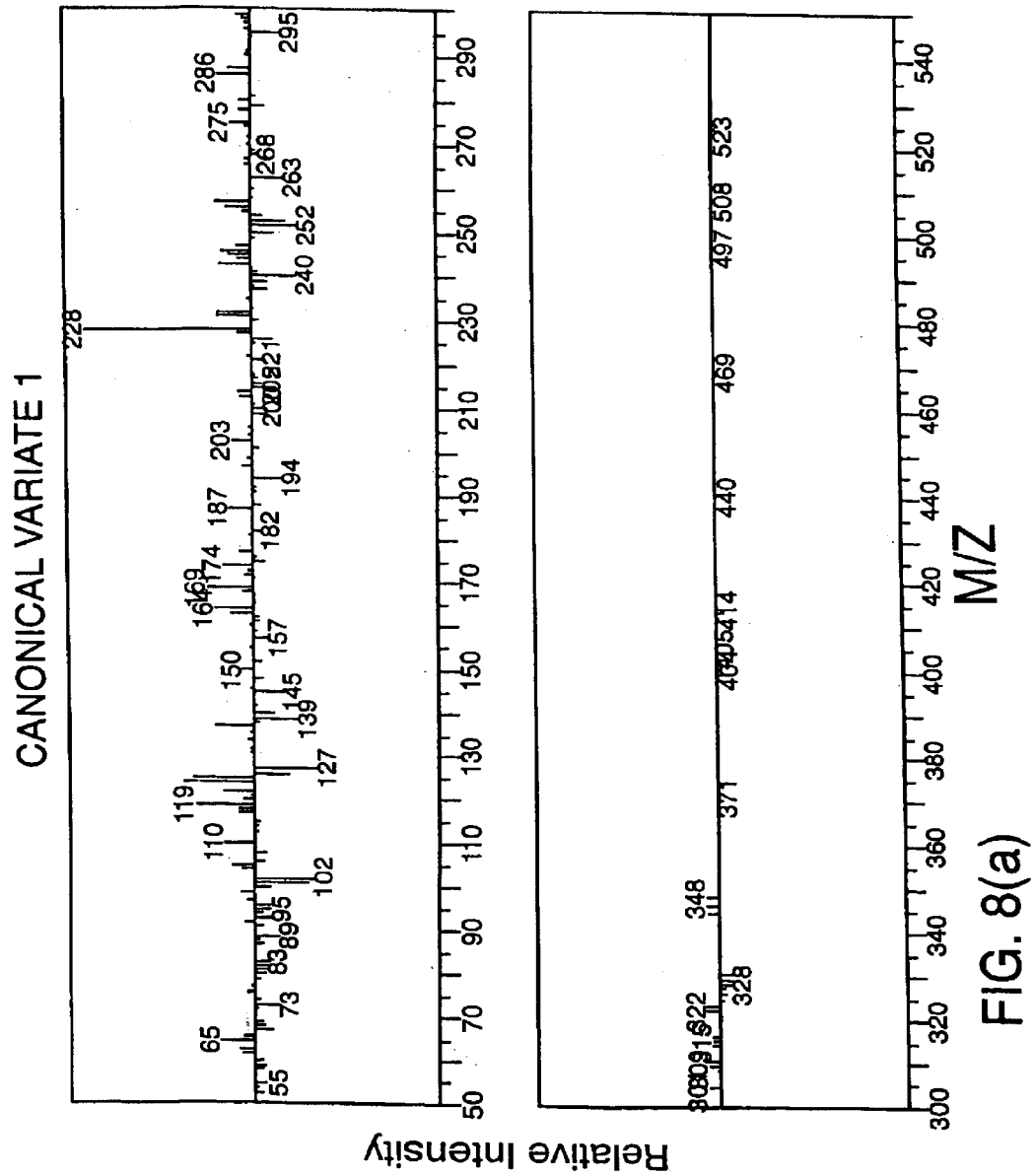
FIGS. 8(a)–8(b) present the first canonical variate factor weights using composite $^{13}$C NMR spectral data and EI mass spectral data for 30 compounds in the SDAR model. The X-axis is the bin number and the Y-axis is the factor weight relative intensity. EI mass spectral data are in the bins numbered from m/z 0 to 550. $^{13}$C NMR spectral data occupies the bins numbered from 550 (corresponding to 0 ppm) to 770 (corresponding to 220 ppm).
Figure 8B:
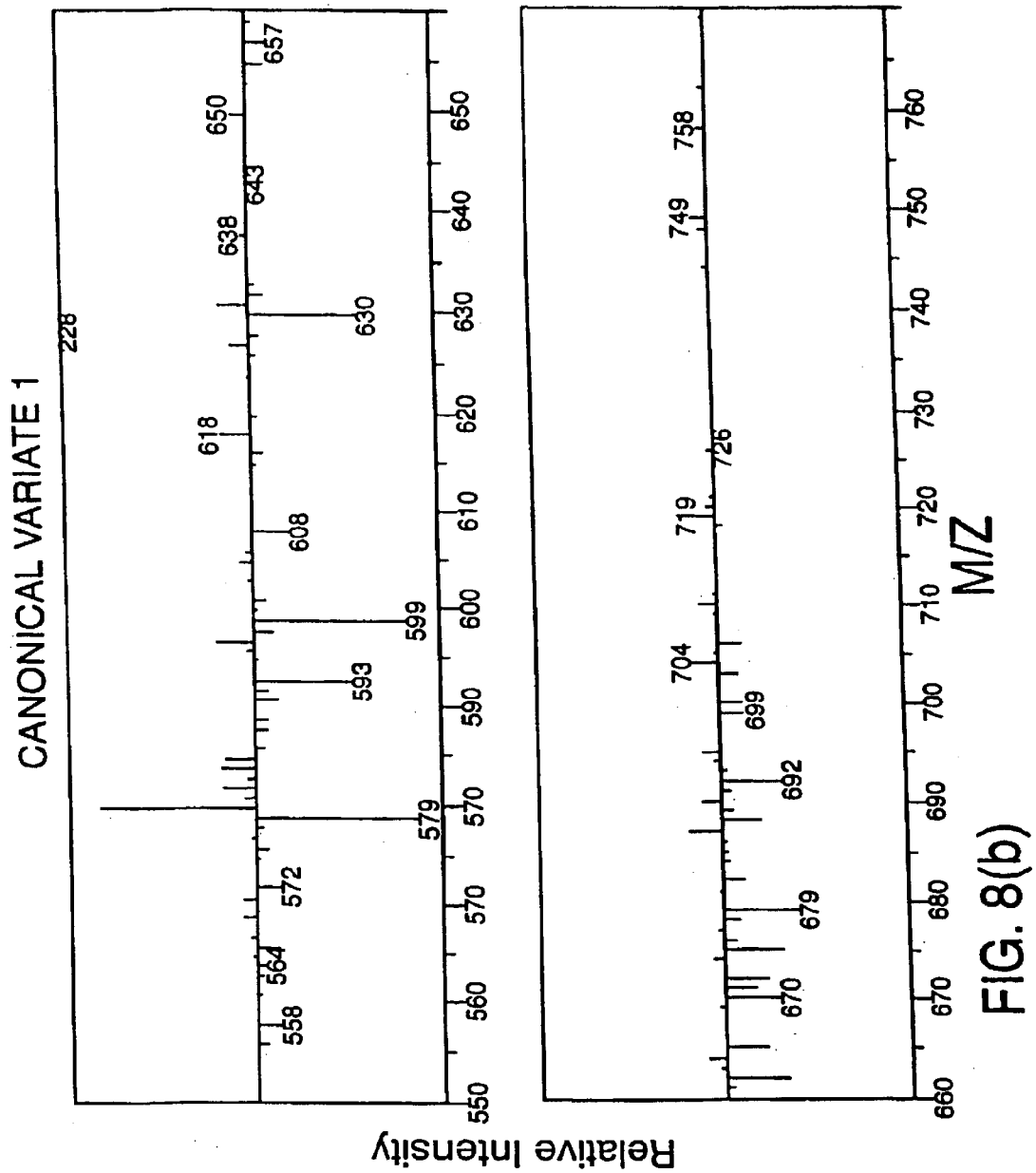

FIG. 8(a) shows the canonical variate function used in the pattern recognition of the EI MS data. FIG. 8(b) shows the canonical variate function used in the pattern recognition of the $^{13}$C NMR data. The negative peaks in FIGS. 8(a) and 8(b) correspond to bins that bias toward a strong relative binder and positive peaks correspond to bins that bias toward a medium relative binder, to the estrogen receptor. In FIGS. 8(a) and 8(b), the label "m/z bins 50 to 550" refers to the EI MS data, whereas "m/z bins 550 to 770" refers to the $^{13}$C NMR data. In FIG. 8(a), the mass canonical variate is split evenly into bins that bias strong and medium binding. Many of the canonical variate bins that showed bias in FIG. 2 are also present in FIG. 8(b), but they are pointing in the opposite direction. The opposite directions found in FIG. 6 and 8(b) are insignificant technically, arising from the pattern-recognition program's arbitrary choice of left and right in the corresponding canonical variate score plot.

Only 3β-androstanediol and hexestrol are incorrectly predicted in both SDAR models. 3β-androstanediol is closest to 3α-androstanediol, 5α-androstanedione, and 5β-androstanedione, all three of which have medium RBAs. Note however, 3β-androstanediol has been inconsistently identified in the literature as a medium estrogen-receptor binder and a strong estrogen-receptor binder (see Miksicek, *J. Steroid. Biochem. Mol. Biol.* 49:153–160, 1994 and Kuiper et al., *Endocrinology* 138:863–870, 1997, respectively).

This example illustrates that, using the present method, compounds can be classified by biological activity based on similarities in the spectral patterns of the test compounds to the spectral patterns of the training set. In particular, additional test compounds can be classified according to their expected biological activity by obtaining the corresponding spectral pattern(s) of the test compound (e.g. NMR and MS patterns). Expected biological activity of the test compound can be predicted by detecting similarities between the spectral pattern of the test compound and the spectral patterns of compounds in the training set that are associated with a known biological activity. Similarities in patterns of the canonical variates associated with an endpoint (e.g. a biological activity such as estrogen receptor binding) derived for the training compounds with patterns in the test compound's segmented spectral data, are then used to predict whether the test compound will share the endpoint.

Example 2

Expanded Trailing Set for Estrogen Receptor Binding SDAR

An expanded training set of 107 compounds of varying estrogen receptor binding affinities was utilized to create an SDAR model from $^{13}$C NMR spectral data and to create an SDAR model from a composite of $^{13}$C NMR spectral data and EI MS spectral data. The training set included weak estrogen receptor binders in addition to strong and medium estrogen receptor binders. Data for the training set was obtained from the following references: Blair et al., *Toxicological Sciences*, 54: 138–153, 2000; Hopert et al., *Environmental Health Perspectives*, 106: 581–586, 1998; Zava and Duwe, *Nutr. Canc.*, 27: 31–40, 1997; and Kuiper et al., *Endocrinology*, 138: 863–870, 1997.

For this model, strong estrogen receptor binders were defined as having log(RBA)>−0.25 and weak estrogen receptor binders were defined as having log(RBA)<−3.0. Medium estrogen receptor binders were defined as having log(RBA) in between. The compound names, the input class ("Class"), the predicted endpoint class based upon $^{13}$C NMR only ("Class predicted NMR"), and the predicted endpoint class based upon $^{13}$C NMR plus EI MS ("Class predicted NMR/MS") for the training set are listed below in Table 2. Except for the increased number of compounds and a change in the mass spectral range utilized, the analysis was performed in the same manner as the analysis in Example 1.

TABLE 2

| Compound | RBA | Class | Class predicted NMR | Class predicted NMR/MS |
|---|---|---|---|---|
| 1,4-Diphenyl-1,3-butadiene | | W | W | W |
| 1,6-Dimethylnaphthalene | | W | W | W |
| 1,8-Octanediol | | W | M | M |
| 2,2'-Dihydroxy4-methoxybenzophene | | W | W | W |
| 2,2'-Methylenebis (4-chlorophenol) | −2.45 | M | M | M |
| 2,4,5-T | | W | W | W |
| 2,4-D | | W | W | W |
| 2,4-Dihydroxybenzophenone | −2.61 | W | W | M |
| 2-Chloro-4-methylphenol | −3.66 | W | W | W |
| 2-Chlorophenol | −3.67 | W | W | W |
| 2-Furaldehyde | | W | W | W |
| 2-OH-Estradiol[3] | | S | S | S |
| 2-Phenylphenol | | W | W | W |
| 2-sec-Butylphenol | −3.54 | W | M | W |
| 3-Phenylphenol | −3.44 | W | M | W |
| 4,4'-Dihydroxybenzophenone | −2.46 | M | W | W |
| 4,4'-Methylenebis (N,N-dimethyl) | | W | W | S |
| 4,4'-Methylenedianiline | | W | W | W |
| 4,4'-Methylene(2,6-ditertbutylphenol) | | W | W | W |
| 4,4'-Sulfonylphenol | −3.07 | W | W | W |
| 4-Benzyloxyphenol | −3.44 | W | W | W |
| 4-Chloro-2-methylphenol | −3.67 | W | W | W |
| 4-Chloro-3-methylphenol | −3.38 | W | M | W |
| 4-Ethylphenol | −4.17 | W | W | W |
| 4-Nonylphenol | −1.45 | M | M | W |
| 4-OH-Estradiol[3] | | S | S | S |

TABLE 2-continued

| Compound | RBA | Class | Class predicted NMR | Class predicted NMR/MS |
|---|---|---|---|---|
| 4-OH-Tamoxifen | 2.24 | S | S | W |
| 4-Phenylphenol | −3.04 | W | W | W |
| 4-Stilbenol |  | W | S | S |
| 4-tert-Amylphenol | −3.26 | W | W | W |
| 4-tert-Butylphenol | −3.61 | W | W | W |
| 4-tert-Octylphenol | −1.82 | M | M | W |
| 5α-Androstane-3α,17β-diol | −2.67 | M | W | M |
| 5α-Androstane-3β,17β-diol | −0.92 | M | W | M |
| Aldrin |  | W | W | M |
| Aurin | −1.49 | M | M | M |
| Benzylalcohol |  | W | W | W |
| Benzylbutyl phthalate |  | W | W | W |
| BIS (2-ethylhexyl) phthalate |  | W | W | S |
| BIS (2-hydroxyphenyl)-methane |  | W | W | W |
| BIS (4-hydroxyphenyl)-methane | −3.02 | W | W | W |
| Bisphenol A | −2.11 | M | M | M |
| Bisphenol B | −1.07 | M | S | M |
| Butyl-4-aminobenzoate |  | W | W | W |
| n-Butylbenzene |  | W | W | M |
| Caffeine |  | W | S | W |
| Cholesterol |  | W | W | M |
| Chrysene |  | W | W | W |
| Chrysin |  | W | M | M |
| Cineole |  | W | W | W |
| Cinnamic acid |  | W | W | W |
| Clomiphene | −0.14 | S | M | W |
| Corticosterone |  | W | W | S |
| Coumestrol[1] |  | S | S | S |
| DDD-o,p' |  | W | W | W |
| DDD-p,p' |  | W | W | W |
| DDE-p,p' |  | W | S | S |
| DDT-o,p' | −2.85 | W | W | W |
| DDT-p,p' |  | W | W | W |
| DES | 2.60 | S | S | S |
| Daidzein[1] |  | M | M | M |
| Dexamethasone |  | W | W | W |
| Dibenzo-18-crown-6 |  | W | W | W |
| Dibutyl phthalate |  | W | W | W |
| Dieldrin |  | W | S | S |
| Dienestrol | 1.57 | S | M | S |
| Diethyl phthalate |  | W | W | W |
| Dihydrotestosterone |  | W | M | W |
| Diisobutyl phthalate |  | W | W | W |
| Dimethyl phthalate |  | W | W | W |
| Diphenolic acid | −3.13 | W | S | S |
| Dopamine |  | W | W | W |
| Estra-1,3,5(10)-trien-3-ol | 1.14 | S | S | W |
| Estra-1,3,5(10)-trien-3,6α,17β-triol | −0.15 | S | S | S |
| Estriol | 0.99 | S | S | S |
| Estrone | 0.86 | S | S | S |
| Ethylcinnamate |  | W | W | W |
| Ethynyl estradiol | 2.28 | S | S | S |
| Etiocholan-17β-ol-3-one |  | W | W | W |
| Eugenol |  | W | W | W |
| Genistein[1,2] |  | M | M | M |
| Heptanal |  | W | W | W |
| Hesperetin[2] |  | W | M | M |
| Hexachlorobenzene |  | W | W | W |
| Hexestrol | 2.48 | S | W | W |
| Hexylalcohol |  | W | W | W |
| ICI-164,384 | 1.16 | S | W | S |
| Isoeugenol |  | W | W | W |
| Kaempferol[2] |  | M | M | M |
| Lindane |  | W | W | S |
| Melatonin |  | W | M | M |
| Mestranol | 035 | S | S | S |
| Methoxychlor | −3.2 | W | W | W |
| Moxestrol | 1.14 | S | S | S |
| Nafoxidine | −0.14 | S | S | S |
| Norethynodrel | −0.65 | M | W | M |
| Phenolphthalein | −1.87 | M | W | W |
| Phenol red | −3.25 | W | W | W |
| Progesterone |  | W | W | W |
| Suberic acid |  | W | W | W |
| Tamoxifen | 0.21 | S | S | S |
| Testosterone |  | W | W | W |
| Triphenylethylene | −2.78 | W | W | W |
| Triphenylphosphate |  | W | W | W |
| Vanillin |  | W | W | W |
| 17α-Estradiol | 0.49 | S | S | S |
| 17β-Estradiol | 2.0 | S | S | S |

All compounds without a number) Blair, R. M.; et al. Toxicological Sciences, 54:138–153, 2000.
[1]Hopert A-C.; et al. Environmental Health Porspectives, 106:581–586 1998.
[2]Zava, D. T.; and Duwe, G. Nutr. Canc., 27:31–40, 1997.
[3]Kuiper et al., Endocrinology 138:863–870, 1997.

Figure 9:
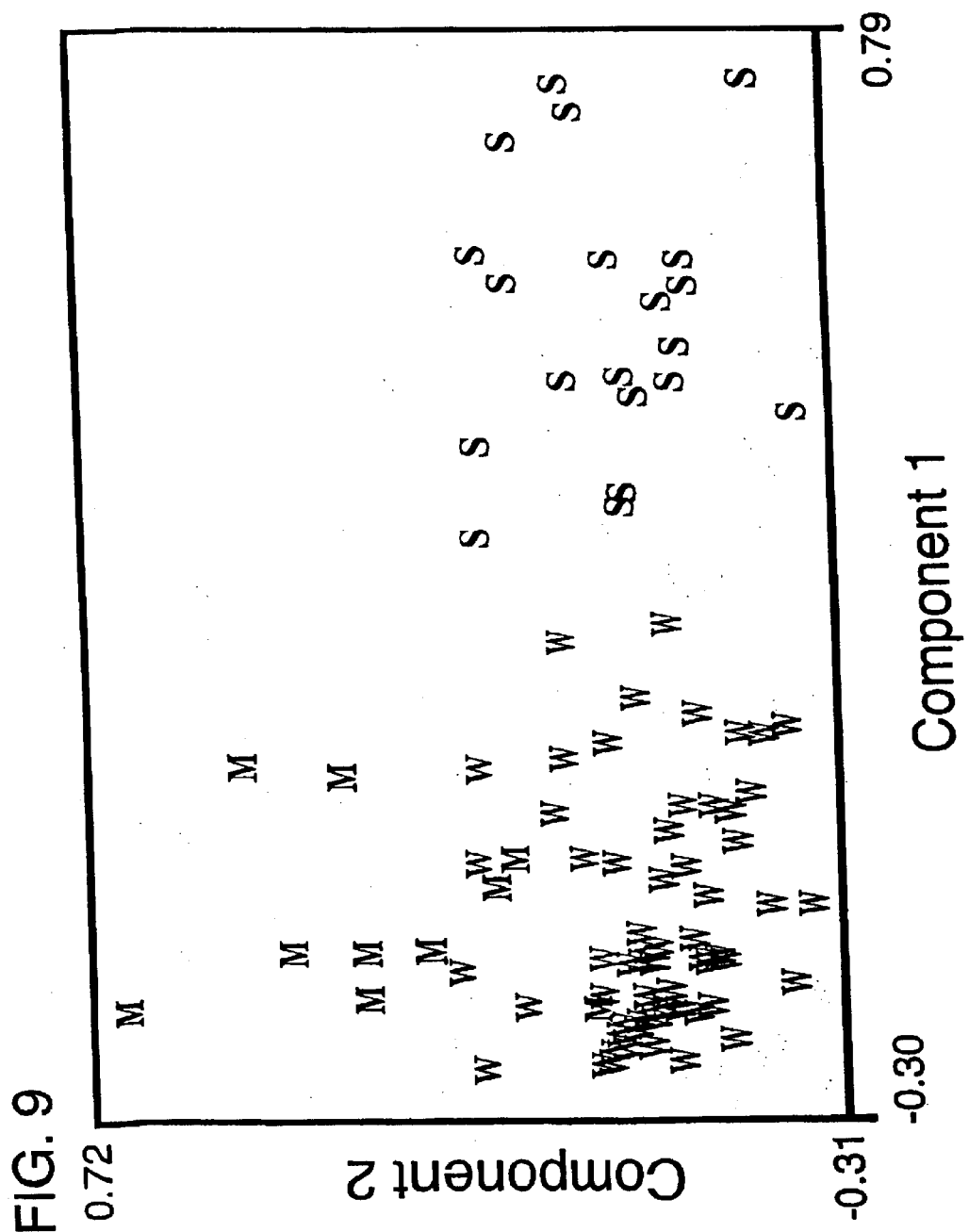
FIG. 9 shows the discriminant function using $^{13}$C Nuclear Magnetic Resonance (NMR) spectral data for 107 compounds in the Spectral Data-Activity Relationship (SDAR) model. The X-axis is the first canonical variate (discriminant function) and the Y-axis is the second canonical variate. The symbol S represents a strong estrogen receptor binder, M represents a medium estrogen receptor binder, and W represents a weak estrogen receptor binder.

Based only on $^{13}$C NMR spectroscopic data, the statistical pattern recognition program with 27 principal components (PCs) had 93.0% of the total variance and a cross validation of 78.5%. FIG. 9 shows the discriminant function for $^{13}$C NMR data of 107 compounds. Compounds that are represented by an S are strong estrogen receptor binders, compounds that are represented by an M are medium estrogen receptor binders, and compounds that are represented by a W are weak estrogen receptor binders. FIG. 9 shows a clustering between the 20 strong, 14 medium, and 73 weak binders. There are cluster overlaps between the weak and strong binders and between the weak and medium cluster region. There are a total of five false positives and three false negatives when using LOO to predict from the 107 compound SDAR model of estrogen receptor binding using only $^{13}$C NMR data.

Figure 10:
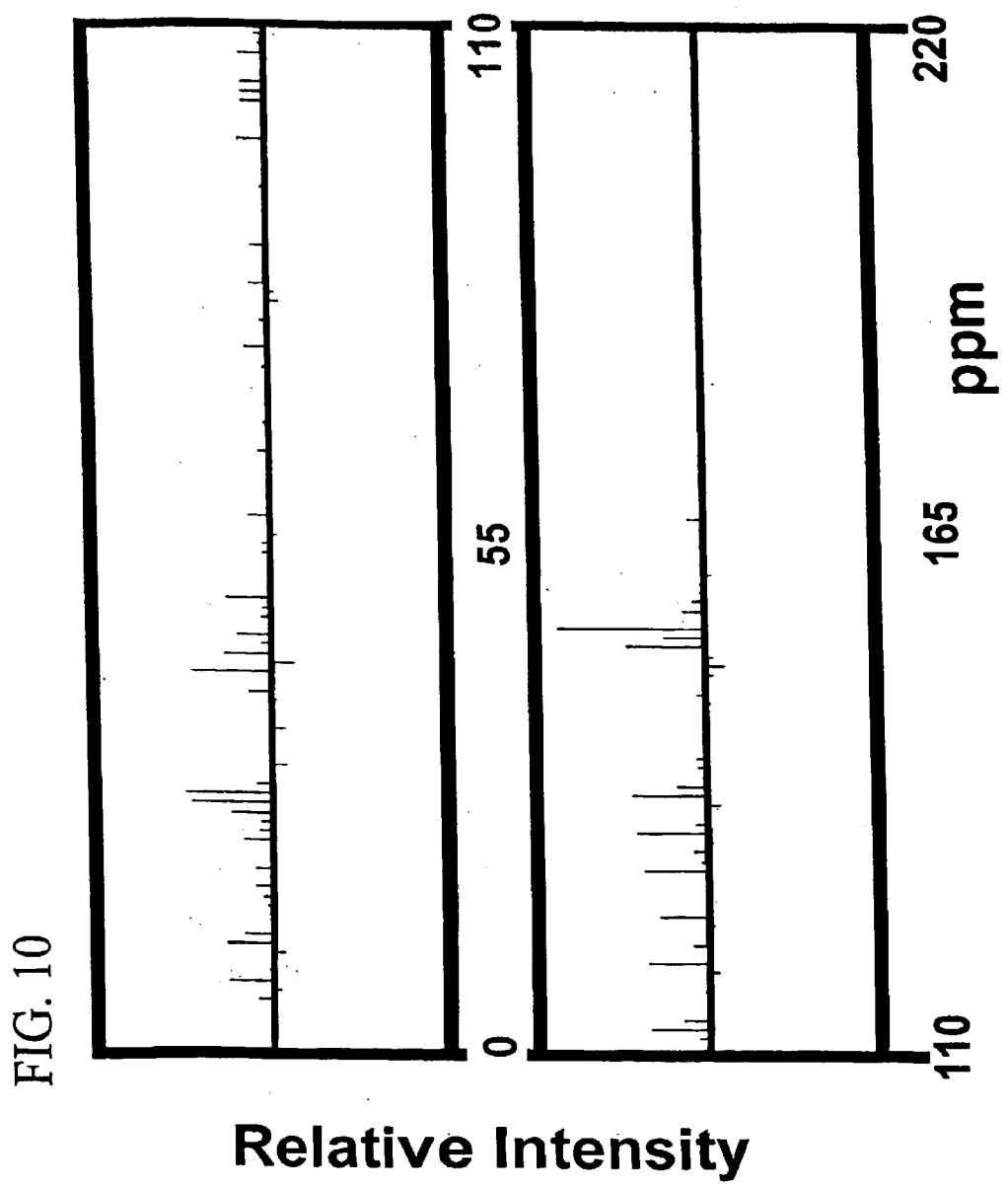
FIG. 10 presents the first canonical variate factor weights using $^{13}$C NMR spectral data for 107 compounds in the SDAR model. The X-axis is the bin number and the Y-axis is the factor weight relative intensity. The bins are numbered from 550 (corresponding to 0 ppm) to 770 (corresponding to 220 ppm).

FIG. 10 shows the factors associated with the first canonical variate function for the pattern recognition of the $^{13}$C NMR data. The positive peaks in FIG. 10 correspond to bins that bias toward a strong RBA for binding to the estrogen receptor and negative peaks correspond to bins that bias toward a medium RBA. In FIG. 10, bins 550 to 770 refer to the $^{13}$C NMR data from 0 ppm for bin 550 to 220 ppm for bin 770. The aliphatic $CH_2$ bins 580 to 585 (30 to 35 ppm) have a bias toward medium RBA. The methyl $CH_3$ bins, such as 558 and 566 (8 and 16 ppm, respectively) have a bias toward strong RBA. Many of the aromatic bins 665 to 700 (115 to 150 ppm) have a bias towards strong RBA.

Figure 11:
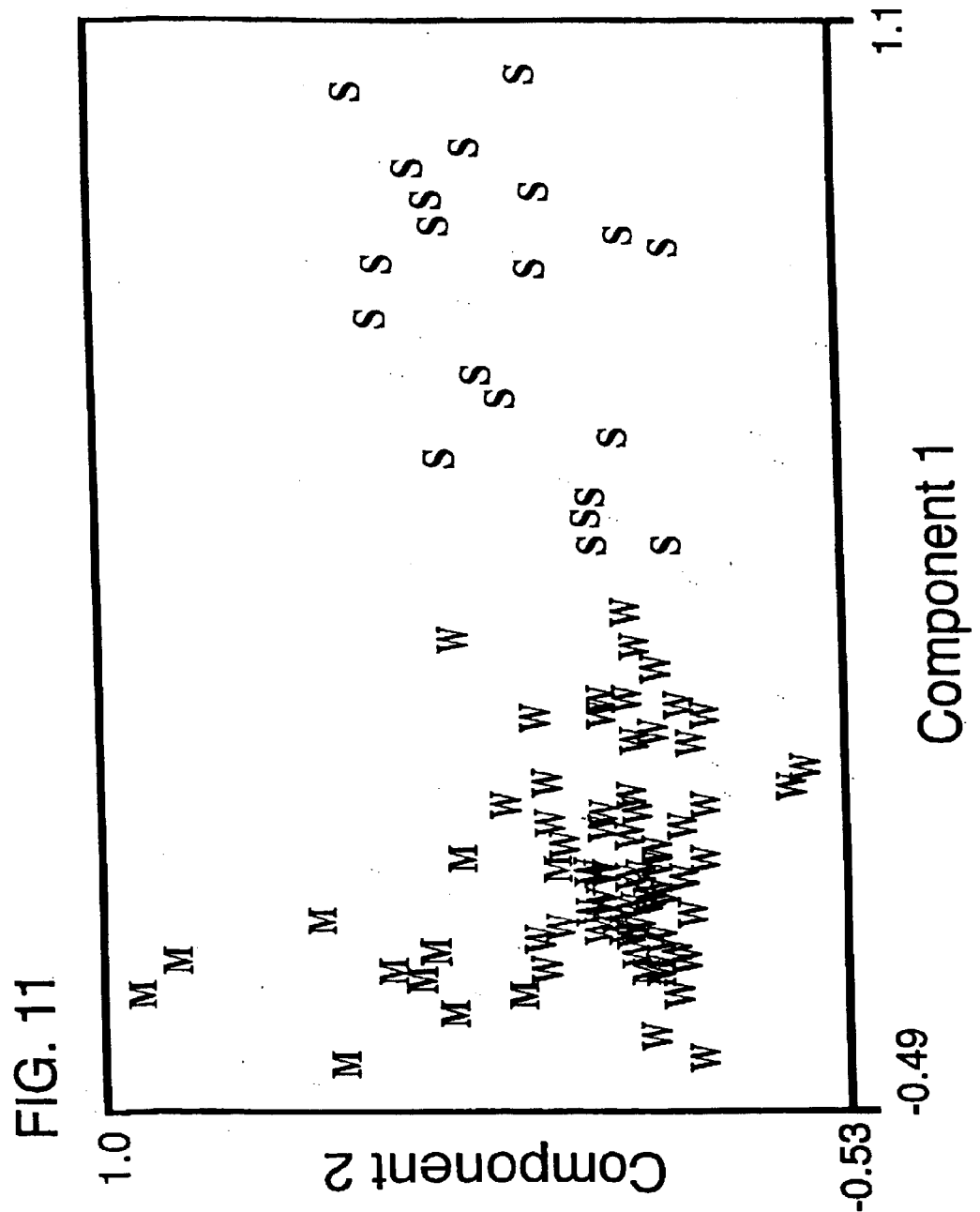
FIG. 11 shows the discriminant function using composite $^{13}$C NMR spectral data and Electron Impact (EI) mass spectral data for 107 compounds in the SDAR model. The X-axis is the first canonical variate and the Y-axis is the second canonical variate. The symbol S represents a strong estrogen receptor binder, M represents a medium estrogen receptor binder, and W represents a weak estrogen receptor binder.

Based on the composite $^{13}$C NMR and EI/MS data over the range m/z=100 to m/z=549, the statistical pattern recognition program with 27 principal components (PCs) included 85.9% of the total variance and had a cross validation of 77.6%. FIG. 11 shows the discriminant function for $^{13}$C NMR data for 107 compounds. The compounds that are shown by an S exhibit strong RBAs, compounds that are shown by an M are exhibit medium RBAs, and compounds that are shown by a W exhibit weak RBAs. FIG. 11 shows a similar clustering between the 20 strong, 14 medium, and 73 weak binders as seen FIG. 9. There are cluster overlaps between the weak and strong binders and between the weak and medium cluster region. There are a total of seven false positives and three false negatives when using LOO to predict a compound's endpoint class from the 107 compound SDAR model of estrogen receptor binding using $^{13}$C NMR and EI/MS data.

Figure 12A:
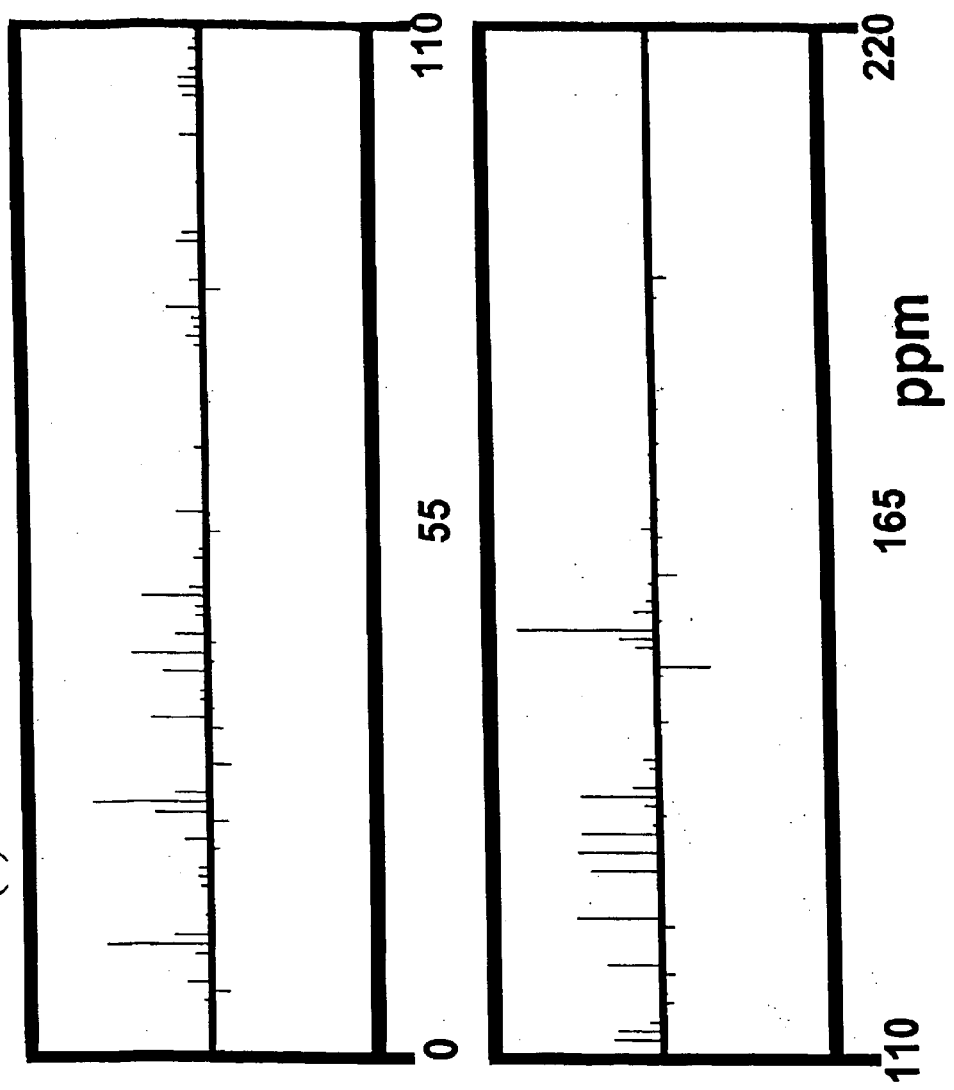
FIGS. 12(a)–12(b) present the first canonical variate factor weights using composite $^{13}$C NMR spectral data and EI mass spectral data for 107 compounds in the SDAR model. The X-axis is the bin number and the Y-axis is the factor weight relative intensity. EI mass spectral data are in the bins numbered from m/z 0 to 550. $^{13}$C NMR spectral data occupies the bins numbered from 550 (corresponding to 0 ppm) to 770 (corresponding to 220 ppm).
Figure 12B:
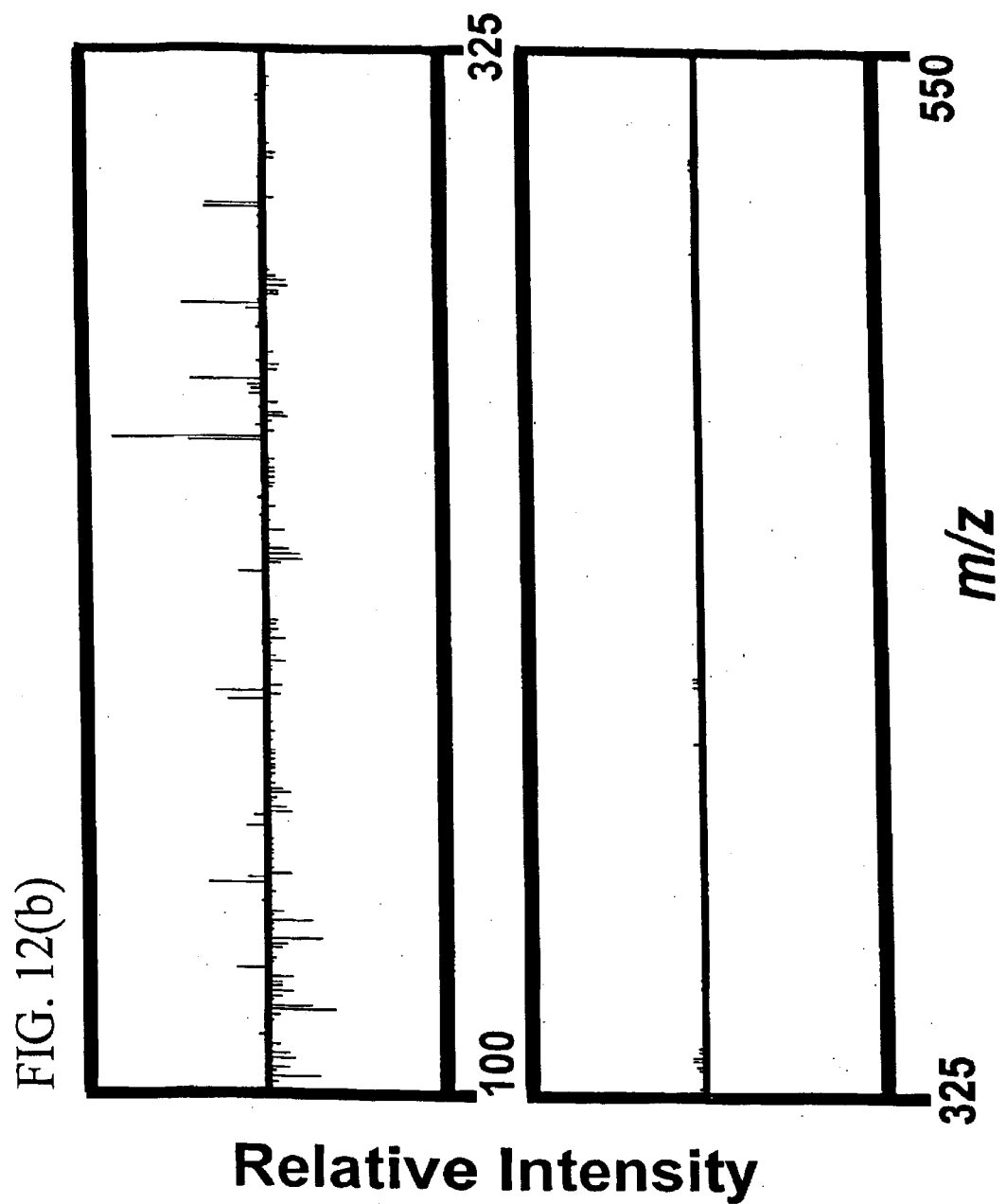

FIGS. 12(a) and 12(b) shows the factors associated with the first canonical variate function for the pattern recognition of the composite $^{13}$C NMR and EI/MS data. The positive peaks in FIGS. 12(a) and 12(b) correspond to bins that bias toward a strong RBA for binding to the estrogen receptor and negative peaks correspond to bins that bias toward a medium RBA. In FIG. 12(a), bins 100 to 549 are the EI/MS data bins and in FIG. 12(b), bins 550 to 770 refer to the $^{13}$C NMR data from 0 ppm for bin 550 to 220 ppm for bin 770. The aliphatic $CH_2$ bins 580 to 585 (30 to 35 ppm) have a bias toward medium RBA. The methyl $CH_3$ bins, such as 558 and 566 (8 and 16 ppm, respectively) have a bias toward strong RBA. Many of the aromatic bins 665 to 700 (115 to 150 ppm) have a bias towards strong RBA.

In both 107 compound SDAR models of estrogen receptor binding, a possible cutoff for testing experimentally whether a molecule did bind to the estrogen receptor would be anything with a positive component 1 as depicted in FIGS. 9 and 11. This would leave no positives untested in each model.

A particularly striking result of the analysis using strong, medium, and weak estrogen receptor binders in the training set is the good separation between strong estrogen receptor binders and the other compounds as seen in FIGS. 9 and 11. There is a marked intermixing of the medium and weak estrogen receptor binders in FIGS. 9 and 11 with respect to the first canonical variate function (X-axis). These results are understandable in light of the physical basis for estrogen receptor binding. Estrogen receptor binding, like most ligand-receptor binding interactions, is governed by specific intermolecular interactions between the ligand and the receptor. The specific intermolecular interactions are what distinguish strong binders from the other compounds. Conversely, there are few or no specific interactions with the receptor on which to distinguish the medium and weak estrogen receptor binders from each other.

Example 3

Use of $^{13}$C NMR, EI MS, and Infrared Spectral Data to Produce a Predictive Model of Biodegradability for Monocyclic Chlorobenzene Derivatives Two recognized factors in the biodegradation of xenobiotic compounds in the environment are the physicochemical properties of the compounds themselves, and the enzymatic activities expressed by the microbial communities in the environment. The vast majority of microbial enzymatic reactions may be classified into one of four categories: 1) group transfer; 2) oxidation and reduction; 3) elimination, isomerization, and rearrangement; and 4) carbon-carbon bond cleavage. The extent to which xenobiotic chemicals can serve as substrates for these enzymatic reactions is determined to a large extent by their structure and particularly by the presence of bonds that are similar to those found in the natural substrates for the enzymes.

Infrared (IR) spectroscopic data may be included in an SDAR to provide a set of spectrally derived structure descriptors that include the types of bonds present in the subject molecules. Infrared data also reflect the modes and frequencies of vibration that are available to subject molecules. As chemical reactions are often tied to particular vibrations of particular bonds, inclusion of the infrared data may improve the ability of an SDAR to predict reactivity.

The biodegradation data for many monocyclic chlorobenzene derivatives in sediment may be found in the Database for Environmental Fate of Chemicals (AIST, Japan). Additional data on the biodegradability is published in *Biodegradation and Bioaccumulation Data of Existing Chemicals Based on the CSCL*, Japan Chemical Industry Ecology-Toxicology & Information Center (JETOC), Tokyo, Japan, 1992. The half-life period is used as the endpoint for the establishment of the SDAR and compounds are classified into two endpoint classes as readily biodegradable (R) (half-life<30 days) and not readily biodegradable (NR) (half-life>30 days). The endpoint data for 34 chlorobenzene derivatives are given in Table 3 below.

TABLE 3

| Compound | Half-life (days) | Input Class |
| --- | --- | --- |
| Monochlorobenzene | 46.2 | NR |
| 1,2-dichlorobenzene | 36.9 | NR |
| 1,3-dichlorobenzene | 433 | NR |
| 1,4-dichlorobenzene | 385 | NR |
| 1,2,3-trichlorobenzene | 23 | R |
| 1,2,4-trichlorobenzene | 40.8 | NR |
| 1,3,5-trichlorobenzene | 35 | NR |
| 1,2,3,4,-tetrachlorobenzene | 18.2 | R |
| 1,2,3,5-tetrachlorobenzene | 18.6 | R |
| 1,2,4,5-tetrachlorobenzene | 28.8 | R |
| Pentachlorobenzene | 17.8 | R |
| Hexachlorobenzene | 27.1 | R |
| 2-chloroaniline | 175 | NR |
| 3-chloroaniline | 672 | NR |
| 4-chloroaniline | 203 | NR |
| 2,3-dichloroaniline | 54 | NR |
| 3,4-dichloroaniline | 55 | NR |
| 3,5-dichloroaniline | 149 | NR |
| 3,4,5-trichloroaniline | 145 | NR |
| 2,3,4,5-trichloroaniline | 57 | NR |
| Pentachloroaniline | 40 | NR |
| 2-chlorophenol | 6.9 | R |
| 3-chlorophenol | 29.2 | R |
| 4-chlorophenol | 11.7 | R |
| 2,3-dichlorophenol | 13.2 | R |
| 2,4-dichlorophenol | 15.3 | R |
| 2,5-dichlorophenol | 46.3 | NR |
| 2,6-dichlorophenol | 5.0 | R |
| 3,4-dichlorophenol | 69.9 | NR |
| 3,5-dichlorophenol | 17.3 | R |
| 2,3,4-trichlorophenol | 1.8 | R |
| 3,4,5-trichlorophenol | 21.7 | R |
| 2,3,4,5-tetrachlorophenol | 6.5 | R |
| Pentachlorophenol | 2.1 | R |

Spectral data for these chlorobenzene compounds is obtained from the Integrated Spectral Data Base System for Organic Compounds (AIST, Japan), the *Aldrich Library of* $^{13}$C *and* $^1$H *FT NMR Spectra* (Poucher and Behnke, Eds., Aldrich Chemical Company, Volumes 1–3, 1993) and the NIST MS database software version 1.6. Experimental $^{13}$C NMR, EI MS, and IR data is collected when spectral data is not available in a database. Experimental spectral data is collected using standard spectroscopic protocols.

The spectral data points are segmented and used in the same way as 3D-QSAR uses comprehensive descriptors for structural and statistical analyses (CODESSA) (See, Tong et al., *J. Med. Chem.*, 39: 380–387, 1995 and Collantes et al., *J. Anal. Chem.*, 68: 2038–2043, 1996, both of which are incorporated herein by reference). Specifically, the $^{13}$C NMR, EI-mass spectral, and IR data are placed into bins. Mass spectrometric data from m/z of 50 to 549 are used. Unassigned ID $^{13}$C NMR chemical shifts are segmented into bins over a 0 to 221 ppm range. The $^{13}$C NMR frequencies are shifted to bins 550 to 770, so bin 550 is the $^{13}$C NMR spectrum for frequencies inside 0 to 1 ppm and bin 770 is the $^{13}$C NMR spectrum for frequencies inside 220 to 221 ppm. The unassigned IR frequencies in the range from 4000 cm$^{-1}$ to 600 cm$^{-1}$ are segmented into bins of 50 cm$^{-1}$ width. The IR data is shifted to bins 771 through 839 so that bin 771 holds the spectral data for the range 4000 cm$^{-1}$ to 3950 cm$^{-1}$ and bin 839 holds the spectral data for the range 650 cm$^{-1}$ to 600 cm$^{-1}$. As an alternative, the IR data may be segmented into ranges of frequency or wavelength rather than the customary wavenumber frequencies.

To save space, the $^{13}$C NMR spectra are saved as sets of ordered pairs, each consisting of the respective chemical shift frequency in ppm and the number of peaks within the frequency range. Likewise, the IR spectra are saved as ordered pairs of bin number and the number of distinct IR peaks appearing in that particular range. Frequency ranges with only one peak are first assigned an area of 1; doubly degenerate frequencies an area of 2; and so forth. This is done to provide all the spectra with similar signal-to-noise ratios and to de-emphasize line-width variations due to differences in experimental conditions. The bin thus defines the number of significant and distinct spectral features within a frequency range. Normalization of the $^{13}$C NMR spectroscopic data and the IR data is accomplished by multiplying each set by a number that makes the maximum value in their respective set of bins equal to 100, which is the maximum value for EI MS data. The number of bins used to input $^{13}$C NMR spectra and IR spectra may be varied to improve the SDAR. Increasing the number of bins and shrinking the frequency width of each bin provides separate bins for closely spaced spectral features that may prove important as structure descriptors for establishing a reliable SDAR.

The segmented $^{13}$C NMR, EI MS, and IR spectral data along with the biodegradability data is input into the pattern recognition program RESolve Version 1.2 (Colorado School of Mines, Boulder, Colo.) and is auto-scaled and Fisher-weighted prior to principal component analysis (PCA). The discriminant analysis is performed based upon the canonical variate vectors. Leave-one-out (LOO) cross-validation is used to maximize the size of the training set. Spectral data for a test compound is then input and the compound judged to be readily biodegradable or not readily biodegradable based upon the presence of a majority of spectral features falling in bins that correspond to canonical variate factors from the training set that bias toward readily biodegradable or not readily biodegradable.

Alternatively, an expert system (self-learning or not) or artificial neural network may be utilized to perform the pattern recognition. Where the endpoint may be the result of multiple underlying mechanisms, such as multiple pathways of biodegradation, expert systems or artificial neural networks may be advantageously utilized to separate compounds based upon their mode of biodegradation in addition to their biodegradatability.

One example of an expert system is the MuRES system that is also part of the RESolve 1.2 software package. The MuRES, package uses spectral data that is first compressed by projection onto a set of principal components. This method of compression is utilitarian, because it reduces the number of variables while maximizing the information content. MuRES uses the spectral scores that are calculated by projecting the spectral data onto a set of eigenvectors. However, MuRES may be applied directly without the compression step to data that already is overdetermined (i.e. more compounds and endpoint values than spectral data structure descriptors).

The knowledge base created by MuRES is in the form of simple binary rules. Binary rules use binary logic, logic that can be only true or false. A complex solution to a problem may be decomposed into a tree, often referred to as a classification tree, which consist of simple binary rules. The largest advantage of the expert system is that the scores do not have to be linearly separable which is an assumption required by discriminant analysis. Further details of the MuRES method are found in Harrington, *RESolve Software Manual*, Colorado School of Mines, Golden Colo., which is incorporated herein by reference.

Example 4

Use of $^{13}$C NMR and UV/Visible Spectroscopic Data to Produce a Predictive Model for the Photosensitized Production of Singlet Molecular Oxygen Phototosensitized oxidations involving singlet oxygen, a strong oxidant, are implicated in photodynamic inactivation of viruses and cells, in phototherapy for cancer, in photo-carcinogenesis and in photodegradation of dyes and polymers. Quenching of excited singlet and triplet states of many substances by ground state molecular oxygen produces singlet oxygen; the lowest electronically excited singlet state of molecular oxygen. A compilation of the quantum yields for the formation of singlet oxygen in fluid solutions for over 700 substances is available from the Notre Dame Radiation Laboratory—Radiation Chemistry Data Center.

Compounds that are capable of photosensitizing the production of singlet oxygen are quite diverse and include aromatic hydrocarbons, aromatic ketones and thiones, quinones, coumarins, fluoresceins, transition metal complexes, and heterocyclics. Porphyrins and pthalocyanines are particularly important classes of compounds that are capable of producing singlet oxygen upon illumination.

To establish an SDAR useful for predicting the ability of molecules to photosensitize the production of singlet oxygen, the quantum yields for production of singlet oxygen by 20 compounds of diverse structure are obtained from the Radiation Chemistry Data Center website. The compounds are divided into two endpoint classes based upon having a high quantum yield for production of singlet oxygen (H, QY>0.50) or a low quantum yield for production of singlet oxygen (L, QY<0.50). Spectral data for these compounds is obtained from the resources mentioned in Examples 1 and 2 or is gleaned from other literature sources or is measured experimentally. The compounds, their singlet oxygen quantum yields, and the endpoint class for each are listed in Table 4.

TABLE 4

| Compound | Quantum Yield | Endpoint Class |
| --- | --- | --- |
| Acetophenone | 0.29 | L |
| Acridine | 0.83 | H |
| Anthracene | 0.83 | H |
| 9,10-Anthraquinone | 0.15 | L |
| Anthrone | 0.25 | L |
| Azulene | 0 | L |
| Benzil | 0.57 | H |
| Benzophenone | 0.29 | L |
| Biacetyl | 0.57 | H |
| Biphenyl | 1.0 | H |
| Flourene | 0.74 | H |
| 1-Methylindole | 0.35 | L |
| 1,3-Diphenylisobenzofuran | 0.26 | L |
| Phenalen-1-one | 0.94 | H |
| Pivalothiophenone | 1.0 | H |
| Psoralen | 0.0055 | L |
| Pyrene | 0.71 | H |
| (E)-Stilbene | 0.08 | L |
| Tetracene | 0.70 | H |
| Xanthen-9-one | 0.33 | L |

Ultraviolet-visible (UV-Vis) spectral data is used along with $^{13}$C NMR spectral data in the SDAR to include a measure of the importance of molecular excited states to the production of singlet oxygen. The segmented spectral data is used as a set of descriptors in the same way that 3D-QSAR uses comprehensive descriptors for structural and statistical analyses. (CODESSA) (See, Tong et al., *J. Med. Chem.*, 39: 380–387, 1995 and Collantes et al., *J. Anal. Chem.*, 68: 2038–2043, 1996, both of which are incorporated herein by reference). The $^{13}$C NMR spectral data is segmented into 1 ppm bins over a 0 to 222 ppm range. The UV-Vis data is segmented into 5 nm bins over the range of 190 nm to 900 nm. The $^{13}$C NMR spectral data occupies bins 1 through 221 and the UV-Vis data occupies bins 222 through 321. To save space, the $^{13}$C NMR spectral data is saved as sets of ordered pairs, each consisting of the bin number and the number of peaks with the frequency range corresponding to the bin. As described above, the $^{13}$C NMR bins define the number of significant and distinct spectral features within a frequency range. The UV-Vis data is saved as sets of ordered pairs, each consisting of the bin number and the average molar absorptivity of the molecule within the wavelength range corresponding to the bin. Molar absorptivity is used rather than absorbance to correct for variations in concentration between the measured UV-Vis spectra of the compounds.

The segmented $^{13}$C NMR and UV-Vis spectral data along with the quantum yields for singlet oxygen production for 20 compounds (the training set) are input as text files into the pattern recognition program RESolve Version 1.2 (Colorado School of Mines, Boulder Colo.). The spectroscopic data is auto-scaled and Fisher-weighted prior to principal component analysis (PCA). The discriminant analysis is performed based upon the canonical variate vectors. Leave-one-out (LOO) cross-validation is used to maximize the size of the training set and measure the ability of the SDAR to classify compounds correctly into their endpoint class. The number of bins used to input $^{13}$C NMR spectral data and UV-Vis spectral data may be varied. Increasing the number of bins will shrink the frequency width of each bin and provide separate bins for closely spaced spectral features that may prove important as structure descriptors for establishing a reliable SDAR. Increasing the number of compounds in the training set may also lead to a more reliable SDAR.

Once the training set has been cross-validated and deemed reliable, test compounds are then subjected to $^{13}$C-NMR and UV/Visible Spectroscopy, and these spectra are segmented into bins in the same manner as with the training set. Spectral patterns in these spectra for the test compound are then compared to the patterns for the training set, and endpoints associated with the spectral patterns of the training set are used to predict endpoints for the test compound. Where the endpoint is photosensitization of singlet oxygen, the presence or absence of spectral patterns in the training set which are associated with that endpoint are then detected to predict whether the test compound would be likely to have that characteristic.

Example 5

Use of an Experimentally Derived SDAR and $^{13}$C NMR Spectral Data to Screen a Combinatorial Library of Compounds for Estrogen Receptor Binding Ability Combinatorial chemistry refers to methods of generating large numbers of compounds from smaller building block compounds that play an important role in generating lead compounds for rational drug design. The building block compounds are allowed to react to yield new compounds, either by mixed synthesis using all building blocks together at once or by sequential reaction of the building block compounds. The reactions can take place within the virtual environment of a computer or they can actually be carried out in a reactor system. The resulting set of compounds is termed a combinatorial library.

A combinatorial library of compounds is produced using a combinatorial chemistry software package such as Afferent Structure™ (Afferent Systems, San Francisco, Calif.). With this software package it is possible to begin with a molecule and perform virtual synthetic steps on that molecule and any intermediate compounds made therefrom to yield a large number of intermediate and final product structures.

For each of the structures generated using the combinatorial chemistry software, $^{13}$C NMR spectra are predicted. The $^{13}$C NMR spectra may be predicted by any known method. Examples of methods for predicting $^{13}$C NMR spectra include the neural network methods described by Kvasnicka (Kvasnicka, V., *J. Math. Chem.*, 6: 63–76, 1991) and the quantum mechanical calculations of Dios et al. (Dios et al., *Science* 260:1491–1496, 1993). Software for predicting $^{13}$C NMR spectra is also available from Advanced Chemistry Development, Toronto, Ontario, Canada (ACD/CNMR Spectrum Generator).

The predicted $^{13}$C NMR spectra are segmented into bins as the experimental $^{13}$C NMR spectra in Example 1 were segmented. The segmented, predicted spectral data is input into the pattern recognition program and the SDAR established for estrogen receptor binding based on $^{13}$C NMR only, from Example 1, is used to classify the compounds in the combinatorial library as either strong or medium estrogen receptor binders. Those compounds predicted by the SDAR to be strong estrogen receptor binders may then be tested experimentally for ability to bind to estrogen receptors.

Combinatorial libraries offer a quick approach to generating large numbers of new compounds, yet screening those compounds for specific biological activities is difficult and time consuming. The methods of the present invention provide rapid methods of screening the products produced by combinatorial chemistry methods so that time consuming assays are performed only on compounds likely to exhibit the desired endpoint properties.

While this embodiment utilized an SDAR generated using experimental spectral data, in another embodiment, calculated spectral data is used to establish the SDAR. An SDAR established with calculated spectral data may be desirable when screening compounds according to their calculated spectral data, as the errors in calculated peak position are advantageously similar in both the training set spectral data and test compound spectral data.

Example 6

Screening of Fractions for Specific Activities using SDAR

The SDAR methods of the present invention are useful for screening raw fractions of compounds derived either from natural sources or from chemical reaction mixtures (including experimental combinatorial libraries).

A biological source of potentially new compounds, such as a sponge, is homogenized and partitioned to provide an aqueous fraction and an organic fraction. Each of these fractions is then chromatographed by any known method to yield a larger number of fractions that contain one or more compounds. Within some of these fractions, a compound or compounds capable of binding to estrogen receptors may be present. SDAR is used to quickly screen the fractions for the presence of estrogen receptor binding compounds.

An unassigned $^{13}$C NMR spectrum is obtained for each fraction and the spectrum is segmented into bins of 1 ppm width. The fraction spectral data is then used along with the SDAR based on $^{13}$C NMR data only, as in Example 1, to predict the fraction's ability to bind to estrogen receptors. Screening of fractions in this manner avoids the time-consuming and costly step of subjecting each fraction to a bioassay.

Those fractions identified as containing compounds having the potential to bind to estrogen receptors may then be subjected to further analysis to reveal the number and identity of the compounds within the fraction.

Example 7

Endpoints

Endpoints for use with the SDAR methods encompass the full range of biological, chemical, and physical properties exhibited by molecules. The methods of the present invention can be used to assist in drug design, biological activity predictions, toxicological predictions, chemical reactivity predictions, and metabolic pathway predictions. An endpoint is any molecular property or activity that can be measured qualitatively or quantitatively. Endpoints may be expressed in absolute or relative terms.

Endpoints may be chosen to establish SDARs that can be used to predict the environmental fate and toxicity of compounds. The ability of compounds to penetrate membranes, bind to enzyme active sites, react with soil, air, or water constituents, bind to soil constituents, hydrolyze, oxidize, and be transported in the environment can be used, along with spectral data for those compounds, to produce useful SDARs.

Spectral data can be used in combination with non-specific measures of toxicity, mutagenicity, teratogenicity, and carcinogenicity to establish SDARs. One example of such a non-specific measure is the Ames test. DNA damage and repair tests, Phosphorous-32 postlabeling, mutation induction in transgenes are others. Yet others include transgenic mouse assays, including the p53 +/− deficient model, the Tg.AC model, the TgHras2 model, and the XPA deficient model. $LD_{50}$ and $EC_{50}$ may provide endpoints for SDAR methods as well. Alternatively, the ability of compounds to induce specific biological outcomes such as cellular changes can be chosen as the endpoint used to establish the SDAR. For example, relevant tissues may be examined for changes at the cellular level using morphological, histochemical, or functional criteria. As appropriate, attention may be directed to such changes as the dose-relationships for apoptosis, cell proliferation, liver foci of cellular alteration, or changes in intercellular communication.

An SDAR may be established based upon any measurable response elicited in animals, plants, and microbes upon exposure to a series of compounds. Examples include SDARs based upon antiviral and antimicrobial activity. The ability of compounds to induce metabolic disorders such as alterations in sugar metabolism may provide a useful endpoint. Phytotoxicity and stimulation of plant growth and reproduction are other examples. Pesticidal activity is yet another example. Measures of anti-hypertensive activity, anti-pyretic activity, anti-depressant activity, and the like further illustrate useful endpoints that are usually related to human health.

Phototoxicity, both specific and non-specific, may be correlated with spectral features to yield an SDAR.

Multiple endpoints may be utilized to establish multiple SDARs from a single set of spectral data. Compounds then may be screened based upon their spectra using multiple SDARs for any combination of desirable or undesirable activities. One example of a useful combination is that of maximal potential efficacy as a therapeutic agent with minimal potential side effects. Agrochemicals may be screened using multiple SDARs for species-specific toxicities and tolerances.

An especially useful application of the methods of the present invention is to the prediction of ligand-target molecule binding. The binding of a molecule to a target such a protein, nucleic acid, synthetic polymer, chimeric molecule, or membrane constituent is often the most important step in the elicitation of a particular property or activity by a molecule. Binding affinities for ligand-target molecule interactions can be expressed in either absolute (e.g., an equilibrium constant) or in relative (e.g., relative to a reference compound, as determined for example by a competitive binding experiment) terms. Example 1 above is one example of how the relative binding affinity of a series of molecules can be utilized along with spectral data to establish a predictive SDAR model. SDAR models based upon relative binding affinities may be useful for rapidly and inexpensively screening compounds for a particular activity. They also may be useful tools for rational drug design when used to identify the spectral, and thus structural, features responsible for that activity.

The metabolic pathway involved in the production or destruction of a series of molecules is another endpoint useful for the methods of the present invention. A predictive SDAR based upon pathway-structure relationships may be able to predict the biosynthetic path for newly discovered naturally occurring compounds. Similarly, SDAR using biodegradability as an endpoint may be useful for predicting the residence time of pollutants in the environment.

Rates of reaction and other measures of reactivity, such as site of reaction on a molecular structure, including the site of electrophilic aromatic substitutions on aromatic compounds, are useful chemical endpoints for the practice of the present invention.

Physical constants such as water-octanol partition coefficients, vapor pressures, pKa, pKb, hydrophobicities, relative acidities and basicities as well as water solubilities can be used with spectral data to provide SDARs. Such estimates may be especially useful for physical properties that are difficult and time-consuming to measure. For example, octanol-water partition coefficients are important for modeling the environmental transport of chemicals. While the octanol-water partition coefficient of a compound might be available, it is less likely that transient species derived from that compound during biodegradation are available in sufficient quantities to measure their octanol-water partition coefficients. SDAR according to the methods of the present invention provides an efficient way to predict the octanol-water partition coefficient for transient species, whose environmental transport characteristics need to be modeled.

Other examples of endpoints useful for the methods of the present invention, in addition to those discussed above, may be found in Hansch and Leo, *Exploring QSAR: Fundamentals and Applications in Chemistry and Biology*, American Chemical Society, 1995. Further examples of endpoints useful for the methods of the present invention may be found in *Quantitative Structure-Activity Relationships in Environmental Sciences-VII*, Chen and Schüürmann, eds., SETAC Press, 1997.

Example 8

Spectral Data

Spectroscopy refers to branch of analytical chemistry in which atomic and molecular structure is studied by measuring radiant energy absorbed or emitted by a substance in any of the wavelengths of the electromagnetic spectrum, in response to excitation by an external energy source. The types of absorption and emission spectroscopy are usually identified by the wavelength involved, such as gamma-ray, X-ray, UV, visible, infrared, microwave, and radiofrequency. Nuclear magnetic resonance spectroscopy (NMR) examines differences in energy states created by a magnetic field. Spectral data refers to the measurements of the energy differences across the spectrum, and spectral patterns refer to differences in the detected energy differences measured across a region of the electromagnetic spectrum. Any instrumental method that produces data that depend upon the structural and quantum mechanical properties of a molecule may be utilized with the methods of the present invention.

Spectral data as used in some embodiments includes the entire spectrum (or spectra) generated by the instrumental method (or methods) of spectroscopy or by calculation. Furthermore, the spectral data need not be assigned to particular structural features. In other embodiments the spectral data comprises only a portion of the spectrum or spectra available. The spectral portions utilized in the methods of the present invention may conveniently cover a spectral region known to typically arise from one or more particular structural features. For example, with respect to $^{13}C$ NMR spectral data, spectral data can be obtained from the entire $^{13}C$ NMR spectrum (0 to 220 ppm), or at least half or a third of that spectrum, or at least a 60 ppm, 80 ppm, 100, or 150 ppm portion of the spectrum. With respect to IR spectral data, for example, the spectral data can be obtained from the entire IR spectrum (4000 $cm^{-1}$ to 500 $cm^{-1}$), or at least a hundredth, fiftieth, quarter, or half of that spectrum, or at least a 35, 50, 100, 200, 500, or 1000 $cm^{-1}$ portion of the spectrum. In particular embodiments, all or substantially all of the spectral data within a particular portion of the spectrum is obtained. However, the spectral features within the entire spectrum of within the portion of the spectrum need not be assigned to structural features and referenced to the corresponding spectral features arising from the structure features of a reference compound. For example, rather than utilizing the assigned $^{13}C$ NMR resonances of the carbon atoms in a substituted benzene ring referenced to the $^{13}C$ NMR resonances of the carbon atoms in unsubstituted benzene, the present invention could utilize the entire spectral region wherein benzene ring carbons typically fall, without assigning and referencing the data therein to the corresponding spectral data for benzene, which has a known structure.

Nuclear magnetic resonance (NMR) data is especially attractive for use with the present invention because of the large amount of structural information contained in a NMR spectrum. NMR instrumentation is widely available and NMR spectra are obtained routinely during structure elucidation. Additionally, the NMR spectra of many compounds have already been measured and are available (see Example 1 for some representative sources).

$^{13}C$ NMR and $^{1}H$ NMR spectral data (especially $^{13}C$ NMR spectral data), are very sensitive to subtle changes in substitution, conformation, chirality, and electronic density. Moreover, changes in $^{13}C$ NMR chemical shifts can occur at a site as many as five carbon atoms removed from the site of the variation. Solvation and proton-exchange effects on the electronic properties of molecules are more clearly reflected in $^{1}H$ NMR chemical shifts and line widths. One-dimensional $^{13}C$ NMR and $^{1}H$ NMR spectral data as well as two-dimensional $^{13}C$-$^{1}H$ heterocorrelation data such as that derived from HSQC and HMQC experiments are useful. Furthermore, modern FT-NMR instruments are capable of providing NMR spectral data for as little as 1 nanogram of a compound (an amount likely insufficient for performing standard bioassays such as the Ames test).

NMR data may be segmented into bins prior to their analysis, along with endpoint data, in a pattern-recognition program. Suitable bin widths will vary according to the identity of the nuclei for which the spectrum is generated, and whether the technique is one or two-dimensional. For one-dimensional $^{13}C$ NMR spectral data, the bin width may be varied from the digital resolution of the instrument (typically about 0.1 ppm) to about 50 ppm. For one-dimensional $^{1}H$ NMR spectral data, the bin width may be varied from the instrumental digital resolution (typically about 0.01 ppm) to about 2 ppm. For two-dimensional $^{13}C$-$^{1}H$ heterocorrelation data, the bin may be defined by similar corresponding widths in both the $^{13}C$ and $^{1}H$ dimensions. Even data of higher dimensions (e.g., three, four, etc.) including NMR spectral data from other nuclei, such as $^{15}N$, $^{31}P$, $^{19}F$, $^{17}O$, and $^{35}S$ may be used in establishing an SDAR. Correspondingly, bins may be defined with respect to each dimension and may be of a width equal to the digital resolution of the data or greater.

In another embodiment of the invention, $^{13}C$ NMR spectral data are predicted by calculation (see, for example, Dios et al., *Science* 260:1491–1496, 1993 and Kvasnicka, V., *J. Math. Chem.*, 6: 63–76, 1991) and used in an SDAR model that has been trained on true $^{13}C$ NMR spectral data Software for predicting $^{13}C$ NMR spectra is also available from Advanced Chemistry Development, Toronto, Ontario, Canada (ACD/CNMR Spectrum Generator). Predicted $^{13}C$ NMR spectral data may be used, for example, to aid in rational drug design by allowing proposed structures to be tested for potential activities before synthesis is attempted.

If predicted spectral data is utilized to establish an SDAR, the spectral data may be segmented into bins that are desirably of a width equal to the average standard deviation in chemical shift predicted by the method, or greater. Likewise, test structure predicted spectra may be segmented in a similar fashion.

Mass spectrometry can provide a measure of the size of a molecule, the size and identity of a molecule's structural subunits, and information regarding bond strengths within a molecule. Mass spectral data, especially electron impact mass spectral (EI MS) data, has already been obtained for many compounds and, even more so than NMR data, is available from convenient sources (see Example 1). EI MS data is also a standard technique used in structure elucidation.

Other mass spectrometric techniques that are useful for providing additional and often complementary information include time-of-flight mass spectrometry (TOF MS), chemical ionization mass spectrometry (CI MS), fast-atom bombardment (FAB). Modern TOF MS spectrometers are capable of providing mass-spectral data from 1 ng or less of purified material (an amount that is likely insufficient for performing standard activity screens such as the Ames test).

Mass spectral data may be segmented into ranges of m/z ratio (for instance, ranges corresponding to mass ranges from about the digital resolution of the instrumental method, typically about 0.1 amu, to about 50 amu) or may be segmented according to integer m/z ratios, with non-integer m/z ratios being rounded to the nearest integer.

Infrared (IR) spectra may also be used, for example in establishing SDAR models capable of discerning differences in activity seen for tautomers that are indistinguishable in NMR and mass spectrometric data. Infrared (IR) spectra are treated in a similar fashion to the NMR spectral data of Example 1 in that each spectrum may be separated into bins of a certain spectral range, for example from about 1 $cm^{-1}$ to about 200 $cm^{-1}$ for entry into a pattern-recognition program Ultraviolet-Visible (UV-Vis) spectral data, which is inherently reflective of the electronic energy levels of a molecule, may be used by segmenting the spectral data into bins of a certain spectral range, for example from about the digital resolution of the instrumental method to about 50 nm. UV-Vis spectral data can be used, for example, in predicting phototoxicity under solar illumination. Similarly, fluorescence and phosphorescence spectra may be handled analogously to UV-Vis spectra and utilized to establish an SDAR. Fluorescence and phosphorescence spectra reflect the energy redistribution within a molecule upon absorption of light and thus may provide important structure descriptors for predicting the light driven properties of molecules.

In addition to the possibility of using a single type of spectral data to establish an SDAR, spectral data of various types may be combined to form composite sets of spectral data. Entire spectra or particular regions of spectra may be combined to yield spectral data sets that may be used in the methods of the present invention, along with endpoint data, to establish the SDAR. Spectral data may come from any composite of NMR, MS, IR, Fluorescence, Phosphorescence, and UV-Vis spectra, including composites of different species of spectra within these broad genera of spectra. Furthermore, different regions of any type of spectrum can be segmented into bins of different sizes so, for example, portions of a spectrum with many closely spaced peaks can be described by narrow spectral bins and portions of a spectrum without many peaks can be described by wide spectral bins.

In some embodiments the spectral data is not used in its raw form to establish an SDAR, but rather the data is subjected to pattern recognition analysis after some sort of pre-treatment to improve the ability of pattern recognition to extract the SDAR. For example normalization may be used to equalize the importance of spectral data derived from different instrumental methods when forming a composite, such as, a composite of MS data and NMR data wherein the maximum signals might be 100 and 1000 respectively. Autoscaling may be used to equalize the importance of inherently weak spectral data with inherently strong spectral data, for example, UV-Vis absorption bands within an absorption spectrum with very different extinction coefficients. Fisher-weighting may be used to emphasize the spectral data that are most important for predicting the endpoint data, such as spectral data found in compounds with a large endpoint values but absent from compounds with small endpoint values.

In general, techniques for pre-treating data include artifact removal and/or linearization, centering, and scaling and weighting. A common form of artifact removal is baseline correction of a spectrum. Common linearizations include the conversion of spectral transmittance into spectral absorbance and the multiplicative scatter correction for diffuse reflectance spectra. Centering, sometimes called mean centering is simply the subtraction of the mean spectral signal at each frequency or m/z from each spectrum. Scaling or weighting involves multiplying all of the spectra by a different scaling factor for each sub-spectral region. This is done to increase or decrease the influence of certain spectral regions or features. A particular example of weighting is Fisher-weighting. Two types of scaling are typically encountered, variance scaling and autoscaling. Further discussion of data pretreatment may be found in Kramer, R., *Chemometric Techniques for Quantitative Analysis*, Marcel Dekker, Inc., 1998. Additional methods for the pre-treatment of data prior to pattern recognition are known in the art and are included in the present invention.

Since spectral data is utilized in some embodiments in the same manner as 3D-QSAR utilizes comprehensive descriptors for structural and statistical analyses (CODESSA) (see, Tong et al., *J. Med. Chem.*, 39: 380–387, 1995 and Collantes et al., *J. Anal. Chem.*, 68: 2038–2043, 1996, both of which are incorporated herein by reference) it is possible to combine the spectrally derived structure descriptors of the present invention with structure descriptors based on bulk measurements (such as the octanol/water partition coefficient) and still retain the ability to produce predictive models without the need for structural knowledge beforehand. Hybrid methods also fall within the scope of the invention wherein the spectrally derived descriptors, which do not require structural knowledge beforehand, may be combined with other structure descriptors that require structural knowledge to produce a larger set of descriptors for use in a predictive model.

Example 9

Pattern-Recognition Programs

Pattern-recognition programs useful for practicing the present invention are of two major types; statistical and artificial intelligence.

Statistical methods include Principal Component Analysis (PCA) and variations of PCA such as linear regression analysis, cluster analysis, canonical variates, and discriminant analysis, soft independent models of class analogy (SIMCA), expert systems, and auto spin (see, for example, Harrington, *RESolve Software Manual*, Colorado School of Mines, 1988, incorporated by reference). Other examples of statistical analysis software available for principal-component-based methods include SPSS (SPSS Inc., Chicago, Ill.), JMP (SAS Inc., Cary N.C.), Stata (Stata Inc., College Station, Tex.) and Cluster.

Artificial intelligence methods include neural networks and fuzzy logic. Neural networks may be one-layer or multilayer in architecture (See, for example, Zupan and Gasteiger, *Neural Networks for Chemisis*, VCH, 1993, incorporated herein by reference). Examples of one-layer networks include Hopfield networks, Adaptive Bidirectional Associative Memory (ABAM), and Kohonen Networks. Examples of Multilayer Networks include those that learn by counter-propagation and back-propagation of error. Artificial neural network software is available from, among other sources, Neurodimension, Inc., Gainesville, Fla. (Neurosolutions) and The Mathworks, Inc., Natick, Mass. (MATLAB Neural Network Toolbox).

Spectral patterns can be analyzed using other approaches. Analog spectral peak patterns may be digitized, and image analysis may used to search for similarities or differences between the spectral patterns of training sets and test compounds

Example 10

Computer Environments for SDAR Methods

The SDAR methods of the present invention may be implemented using a single computer or utilizing a distributed computing environment.

Exemplary Distributed Computing Environment

Figure 13:
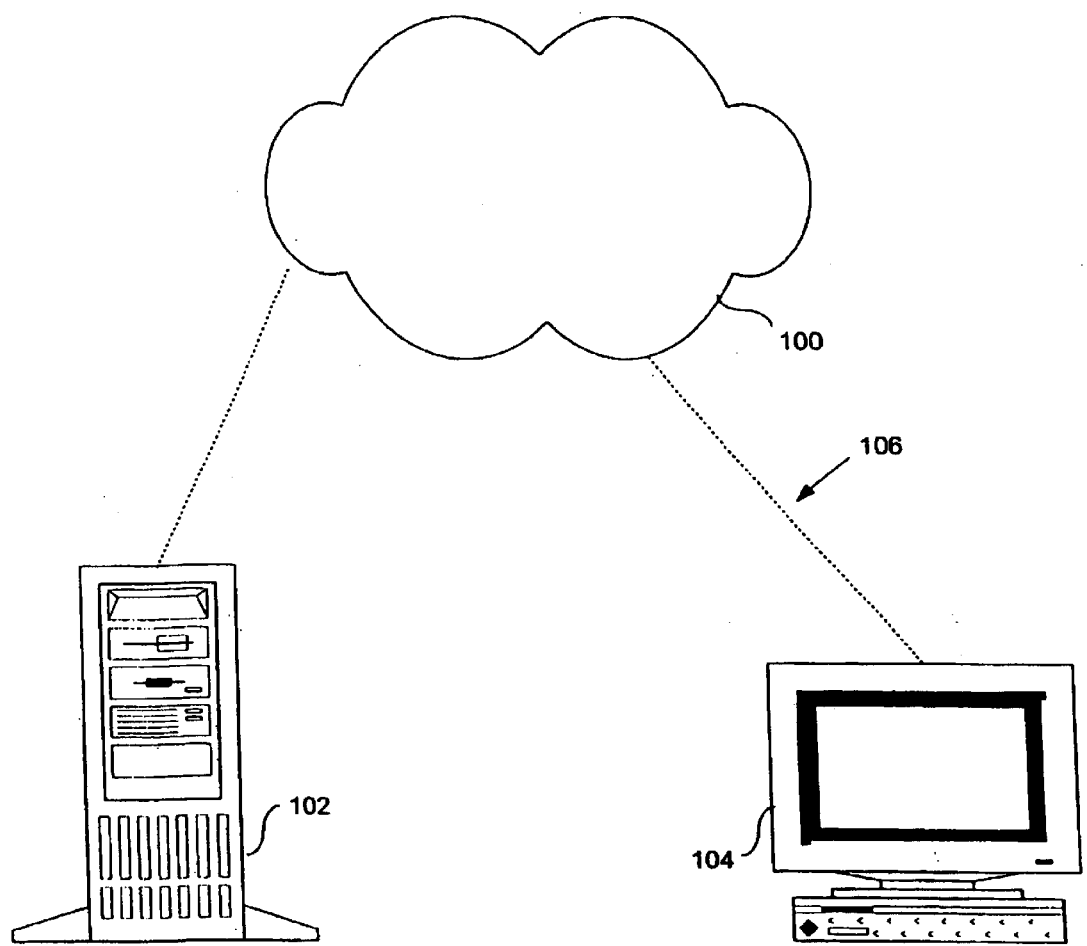
FIG. 13 is a diagram of a distributed computing environment in which the present invention can be implemented.

FIG. 13 illustrates a distributed computing environment in which the software elements used to implement the SDAR methods of the present invention may reside. The distributed computing environment 100 includes two computer systems 102, 104 connected by a connection medium 106. The computer systems 102, 104 can be any of several types of computer system configurations, including personal computers, multiprocessor systems, and the like. In terms of logical relation with other computer systems, a computer system can be a client, a server, a router, a peer device, or other common network node. Moreover, although FIG. 13 illustrates two computer systems 102, 104, the present invention is equally applicable to an arbitrary, larger number of computer systems connected by the connection medium 106. Additional computer systems 102 or 104 may be connected by an arbitrary number of connection mediums 106. The connection medium 106 can comprise any local area network (LAN), wide area network (WAN), or other computer network, including but not limited to Ethernets, enterprise-wide computer networks, intranets and the Internet.

Portions of the SDAR software can be implemented in a single computer system 102 or 104, with the application later distributed to other computer systems 102, 104 in the distributed computing environment 100. Portions of the SDAR software may also be practiced in a distributed computing environment 100 where tasks are performed by a single computer system 102 or 104 acting as a remote processing device that is accessed through a communications network, with the distributed application later distributed to other computer systems in the distributed computing environment 100. In a networked environment, program modules comprising the SDAR software can be located on more than one computer system 102 or 104. Communication between the computer systems in the distributed computing network may advantageously include encryption of the communicated data.

Exemplary Computer System

Figure 14:
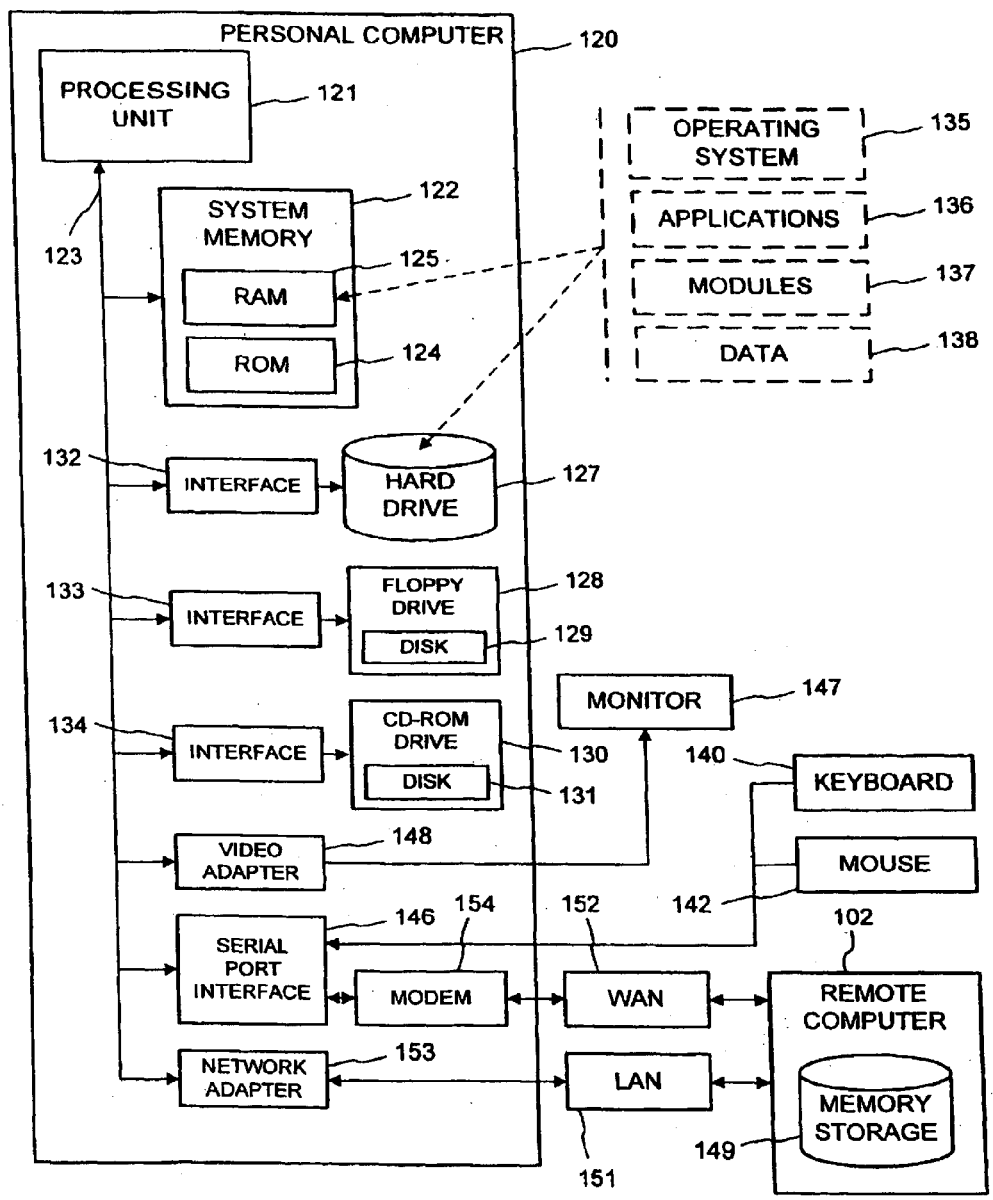
FIG. 14 is a block diagram of a computer system that can be used to implement the present invention.

FIG. 10 illustrates an example of a computer system 120 that can serve as an operating environment for the SDAR software. With reference to FIG. 14 an exemplary computer system for implementing the invention includes a computer 120 (such as a personal computer, laptop, palmtop, set-top, server, mainframe, and other varieties of computer), including a processing unit 121, a system memory 122, and a system bus 123 that couples various system components including the system memory to the processing unit 121. The processing unit can be any of various commercially available processors, including Intel x86, Pentium and compatible microprocessors from Intel and others, including Cyrix, AMD and Nexgen; Alpha from Digital; MIPS from MIPS Technology, NEC, IDT, Siemens, and others; and the PowerPC from IBM and Motorola. Dual microprocessors and other multi-processor architectures also can be used as the processing unit 121.

The system bus can be any of several types of bus structure including a memory bus or memory controller, a peripheral bus, and a local bus using any of a variety of conventional bus architectures such as PCI, VESA, AGP, Microchannel, ISA and EISA, to name a few. The system memory includes read only memory (ROM) 124 and random access memory (RAM) 125. A basic input/output system (BIOS), containing the basic routines that help to transfer information between elements within the computer 120, such as during start-up, is stored in ROM 124.

The computer 120 further includes a hard disk drive 127, a magnetic disk drive 128, e.g., to read from or write to a removable disk 129, and an optical disk drive 130, e.g., for reading a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of data, data structures, computer-executable instructions, etc. for the computer 120. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment.

A number of the SDAR program modules can be stored in the drives and RAM 125, including an operating system 135, one or more application programs 136, other program modules 137, and program data 138.

A user can enter commands and information into the computer 120 through a keyboard 140 and pointing device, such as a mouse 142. Other input devices (not shown) can include a microphone, satellite dish, scanner, or the like. These and other input devices are often connected to the processing unit 121 through a serial port interface 146 that is coupled to the system bus, but can be connected by other interfaces, such as a parallel port, game port or a universal serial bus (USB). A monitor 147 or other type of display device is also connected to the system bus 123 via an interface, such as a video adapter 148. In addition to the monitor, computers typically include other peripheral output devices (not shown), such as printers.

The computer 120 can operate in a networked environment using logical connections to one or more other computer systems, such as computer 102. The other computer systems can be servers, routers, peer devices or other common network nodes, and typically include many or all of the elements described relative to the computer 120, although only a memory storage device 149 has been illustrated in FIG. 14. The logical connections depicted in FIG. 10 include a local area network (LAN) 151 and a wide area network (WAN) 152. Such networking environments are common in offices, enterprise-wide computer networks, intranets and the Internet.

When used in a LAN networking environment, the computer 120 is connected to the local network 151 through a network interface or adapter 153. When used in a WAN networking environment, the computer 120 typically includes a modem 154 or other means for establishing communications (e.g., via the LAN 151 and a gateway or proxy server 155) over the wide area network 152, such as the Internet. The modem 154, which can be internal or external, is connected to the system bus 123 via the serial port interface 146. In a networked environment, program modules depicted relative to the computer 120, or portions thereof, can be stored in the remote memory storage device.

It will be appreciated that the network connections shown are exemplary and other means of establishing a communications link between the computer systems (including an Ethernet card, ISDN terminal adapter, ADSL modem, 10BaseT adapter, 100BaseT adapter, ATM adapter, or the like) can be used.

In accordance with the practices of persons skilled in the art of computer programming, a particular embodiment of the SDAR method is described in FIG. 4 with reference to acts and symbolic representations of operations that may be performed by the computer 120. Such acts and operations are sometimes referred to as being computer-executed. It will be appreciated that the acts and symbolically represented operations include the manipulation by the processing unit 121 of electrical signals representing data bits which causes a resulting transformation or reduction of the electrical signal representation, and the maintenance of data bits at memory locations in the memory system (including the system memory 122, hard drive 127, floppy disks 129, and CD-ROM 131) to thereby reconfigure or otherwise alter the computer system's operation, as well as other processing of signals. The memory locations where data bits are maintained are physical locations that have particular electrical, magnetic, or optical properties corresponding to the data bits.

In view of the many possible embodiments to which the principles of our invention may be applied, it should be recognized that the illustrated embodiments are only specific examples of the invention and should not be taken as a limitation on the scope of the invention. Rather, the scope of the invention is defined by the following claims. We therefore claim as our invention all that comes within the scope and spirit of these claims.

We claim:

1. A method of predicting a biological activity of a test compound, comprising:
   obtaining spectral data for the test compound and for a training set of compounds having known biological activities;
   segmenting the spectral data of the training set of compounds into bins;
   scaling the segmented spectral data of the training set of compounds prior to establishing a spectral data-activity relationship;
   weighting the segmented spectral data of the training set of compounds prior to establishing the spectral data-activity relationship to more heavily weight bins associated with the biological activity;
   establishing the spectral data-activity relationship between the known biological activities and the segmented, scaled and weighted spectral data of the training set of compounds using computer implemented pattern recognition;
   segmenting the spectral data of the test compound into bins to provide segmented spectral data for the test compound; and
   predicting the biological activity of the test compound from the segmented spectral data for the test compound using the spectral data-activity relationship.

2. The method of claim 1, wherein the spectral data are obtained without first correlating the spectral data with corresponding structural features.

3. The method of claim 1, wherein the spectral data-activity relationship is established without first correlating the spectral data with corresponding structural features.

4. The method of claim 1, wherein the spectral data of the test compound is segmented into substantially the same bins as the spectral data of the training set.

5. The method of claim 1, wherein the spectral data is one type of spectral data.

6. The method of claim 5, wherein the spectral data is one of nuclear magnetic resonance, mass spectral, infrared, ultraviolet-visible, fluorescence, or phosphorescence data.

7. The method of claim 1, wherein the spectral data is a composite of different types of spectral data.

8. The method of claim 7, wherein the composite comprises two or more of the group consisting of nuclear magnetic spectroscopy (NMR), mass spectroscopy (MS), infrared (IR) spectroscopy, and ultraviolet-visible (UV-Vis) spectroscopy.

9. The method of claim 1, wherein segmenting the spectral data of the test compound comprises segmenting into substantially the same spectral sub-units as the segmented spectral data of the training set of compounds.

10. The method of claim 1, wherein establishing and predicting comprises statistical pattern recognition.

11. A computer readable medium having stored thereon computer-executable instructions for performing the method of claim 1.

12. The method of claim 1, wherein the spectral data comprises calculated spectral data.

13. The method of claim 1, wherein the spectral data comprises $^1$H, $^{13}$C, $^{15}$N, $^{17}$O, $^{19}$F, $^{31}$P or $^{35}$S NMR data.

14. The method of claim 13, wherein the spectral data comprises calculated spectral data.

15. The method of claim 1, wherein the spectral data of the test compound and the spectral data of the training set of compounds comprise $^{13}$C NMR data, and segmenting the spectral data of the training set into bins and segmenting the spectral the test compound into bins comprise dividing the $^{13}$C NMR data into sub-spectral units having a width from 0.5 ppm to 5.0 ppm.

16. A method of predicting a biological activity of a test compound, comprising:
   obtaining spectral data for the test compound and for a training set of compounds having known biological activities:
   segmenting the spectral data of the training set of compounds into bins;
   auto-scaling the segmented spectral data of the training set of compounds prior to establishing a spectral data-activity relationship;
   weighting the segmented spectral data of the training set of compounds prior to establishing the spectral data-activity relationship;
   establishing the spectral data-activity relationship between the known biological activities and the segmented, scaled and weighted spectral data of the training set of compounds using computer implemented pattern recognition;
   segmenting the spectral data of the test compound into bins to provide segmented spectral data for the test compound; and
   predicting the biological activity of the test compound from the segmented spectral data for the test compound using the spectral data-activity relationship.

17. The method of claim 16, wherein the spectral data comprises $^1$H, $^{13}$C, $^{15}$N, $^{17}$O, $^{19}$F, $^{31}$P or $^{35}$S NMR data.

18. The method of claim 16, wherein the spectral data comprises calculated spectral data.

19. The method of claim 18, wherein the calculated spectral data comprises $^1$H, $^{13}$C, $^{15}$N, $^{17}$O, $^{19}$F, $^{31}$P or $^{35}$S NMR data.

20. A method of predicting a biological activity of a test compound, comprising:

obtaining spectral data for the test compound and for a training set of compounds having known biological activities;

segmenting the spectral data of the training set of compounds into bins;

scaling the segmented spectral data of the training set of compounds prior to establishing a spectral data-activity relationship;

Fisher-weighting the segmented spectral data of the training set of compounds prior to establishing the spectral data-activity relationship;

establishing the spectral data-activity relationship between the known biological activities and the segmented, scaled and weighted spectral data of the training set of compounds using computer implemented pattern recognition;

segmenting the spectral data of the test compound into bins to provide segmented spectral data for the test compound; and predicting the biological activity of the test compound from the segmented spectral data for the test compound using the spectral data-activity relationship.

21. The method of claim 20, wherein scaling comprises variance-scaling.

22. The method of claim 20, wherein scaling comprises auto-scaling.

23. The method of claim 20, wherein the spectral data comprises $^1$H, $^{13}$C, $^{15}$N, $^{17}$O, $^{19}$F, $^{31}$P or $^{35}$S NMR data.

24. The method of claim 20, wherein the spectral data comprises calculated spectral data.

25. The method of claim 24, wherein the calculated spectral data comprises $^1$H, $^{13}$C, $^{15}$N, $^{17}$O, $^{19}$F, $^{31}$P or $^{35}$S NMR data.

26. A method of predicting a biological activity of a test compound, comprising:

obtaining spectral data for the test compound and for a training set of compounds having known biological activities;

segmenting the spectral data of the training set of compounds into bins;

scaling the segmented spectral data of the training set of compounds prior to establishing a spectral data-activity relationship;

weighting the segmented spectral data of the training set of compounds prior to establishing the spectral data-activity relationship;

establishing the spectral data-activity relationship between the known biological activities and the segmented, scaled and weighted spectral data of the training set of compounds using computer implemented artificial intelligence pattern recognition;

segmenting the spectral data of the test compound into bins to provide segmented spectral data for the test compound; and predicting the biological activity of the test compound from the segmented spectral data for the test compound using the spectral data-activity relationship and computer implemented artificial intelligence pattern recognition.

27. A computer implemented method for predicting a biological activity of a test compound, comprising:

receiving spectral data for a test compound as input;

receiving spectral data and endpoint data of a training set of compounds having known biological activities as input;

segmenting the spectral data of the training set of compounds into sub-spectral units;

auto-scaling the segmented spectral data of the training set of compounds;

Fisher-weighting the segmented spectral data of the training set of compounds;

establishing a spectral data-activity relationship between the segmented, scaled and weighted spectral data and the known biological activities of the training set of compounds using pattern recognition;

segmenting the spectral data of the test compound to provide segmented spectral data for the test compound; and predicting the biological activity of the test compound from the segmented spectral data for the test compound using the spectral data-activity relationship.

28. The computer implemented method of claim 27, wherein establishing and predicting are performed with a statistical pattern recognition program.

29. The computer implemented method of claim 28, wherein the spectral data for the test compound is segmented into substantially identical sub-spectral units as the training set spectral data.

30. The computer implemented method of claim 27, wherein the spectral data are selected from the group consisting of nuclear magnetic resonance data, mass spectral data, infrared data, ultraviolet-visible data, fluorescence data, phosphorescence data, and composites thereof.

31. The computer implemented method of claim 30, wherein the spectral data-activity relationship comprises canonical variate factors.

32. The computer implemented method of claim 31, wherein the biological activity is binding affinity to a hormone receptor.

33. The computer implemented method of claim 32, wherein the spectral data comprise nuclear magnetic resonance data and mass spectral data.

34. A computer readable medium having stored thereon computer-executable instructions for performing the method of claim 27.

35. The computer implemented method of claim 27, wherein the spectral data comprises calculated spectral data.

36. The computer implemented method of claim 35, wherein the calculated spectral data comprises calculated nuclear magnetic resonance data.

37. The computer implemented method of claim 36, wherein the calculated nuclear magnetic resonance data comprises calculated $^{13}$C NMR data.

38. The method of claim 36, wherein the calculated nuclear magnetic resonance data comprises $^1$H, $^{13}$C, $^{15}$N, $^{17}$O, $^{19}$F, $^{31}$P or $^{35}$S NMR data.

39. A method of predicting a biological activity of a test compound, comprising:

obtaining spectral data for the test compound and for a training set of compounds having known biological activities;

segmenting the spectral data of the training set of compounds into bins;

scaling the segmented spectral data of the training set of compounds prior to establishing a spectral data-activity relationship;

weighting the segmented spectral data of the training set of compounds prior to establishing the spectral data-activity relationship;

establishing the spectral data-activity relationship between known biological activities and the segmented, scaled and weighted spectral data of the training set of compounds using computer implemented pattern recognition;

segmenting the spectral data of the test compound into bins to provide segmented spectral data for the test compound;

predicting the biological activity of the test compound from segmented spectral data for the test compound using the spectral data-activity relationship; and predicting a second biological activity of the test compound using a second spectral data-activity relationship, the second spectral data-activity relationship established between the scaled and weighted spectral data of a second training set of compounds and the known biological activities of the second training set compounds.

40. A method for predicting a biological property of a test compound, comprising:

providing spectral data for a training set of compounds having known biological activities;

providing spectral data for the test compound;

segmenting the spectral data for the test compound into bins to provide segmented spectral data for the test compound;

segmenting the spectral data for the training set of compounds into bins;

scaling the spectral data of the training set of compounds in the bins;

weighting the spectral data of the training set of compounds in the bins to more heavily weight bins associated with the biological property;

establishing a spectral data-activity relationship between the known biological activities and the segmented, scaled and weighted spectral data of the training set of compounds using computer implemented statistical pattern recognition; and using the spectral data-activity relationship to predict the biological activity of the test compound from the segmented, scaled and weighted spectral data of the test compound.

41. The method of claim 40, wherein the spectral data comprises nuclear magnetic resonance, mass spectral, infrared, ultraviolet-visible, fluorescence, phosphorescence data, or composites thereof.

42. The method of claim 41, wherein the spectral data comprises $^{13}C$ NMR data.

43. The method of claim 42, wherein the $^{13}C$ NMR data comprises calculated $^{13}C$ NMR data.

44. The method of claim 41, wherein the spectral data comprises $^{13}C$ NMR data and EI-MS data.

45. The method of claim 40, wherein detecting a pattern comprises statistical pattern recognition.

46. A method for predicting a biological property of a test compound, comprising:

providing spectral data for a training set of compounds having known biological activities:

providing spectral data for the test compound;

segmenting the spectral data for the test compound into bins to provide segmented spectral data for the test compound;

segmenting the spectral data for the training set of compounds into bins;

auto-scaling the spectral data of the training set of compounds in the bins;

weighting the spectral data of the training set of compounds in the bins;

establishing a spectral data-activity relationship between the known biological activities and the segmented, scaled and weighted spectral data of the training set of compounds using computer implemented statistical pattern recognition; and using the spectral data-activity relationship to predict the biological activity of the test compound from the segmented spectral data of the test compound.

47. The method of claim 46, wherein weighting comprises Fisher-weighting.

48. A method for predicting a biological property of a test compound, comprising:

providing spectral data for a training set of compounds having known biological activities;

providing spectral data for the test compound;

segmenting the spectral data for the test compound into bins to provide segmented spectral data for the test compound;

segmenting the spectral data for the training set of compounds into bins;

scaling the spectral data of the training set of compounds in the bins;

Fisher-weighting the spectral data of the training set of compounds in the bins;

establishing a spectral data-activity relationship between the known biological activities and the segmented, scaled and weighted spectral data of the training set of compounds using computer implemented statistical pattern recognition; and using the spectral data-activity relationship to predict the biological activity of the test compound from the segmented spectral data for the test compound.

49. A method for predicting a biological property of a test compound, comprising:

providing spectral data for a training set of compounds having known biological activities;

providing spectral data for the test compound;

segmenting the spectral data for the test compound into bins to provide segmented spectral data for the test compound;

segmenting the spectral data for the training set of compounds into bins;

variance scaling the spectral data of the training set of compounds in the bins;

weighting the spectral data of the training set of compounds in the bins;

establishing a spectral data-activity relationship between the known biological activities and the segmented, scaled and weighted spectral data of the training set of compounds using computer implemented statistical pattern recognition; and using the spectral data-activity relationship to predict the biological activity of the test compound from the segmented spectral data for the test compound.

50. A method for predicting a biological property of a test compound, comprising:

providing spectral data for a training set of compounds having known biological activities;

providing spectral data for the test compound;

segmenting the spectral data for the test compound into bins to provide segmented spectral data for the test compound;

segmenting the spectral data for the training set of compounds into bins;

scaling the spectral data of the training set of compounds in the bins;

weighting the spectral data of the training set of compounds in the bins;

establishing a spectral data-activity relationship between the known biological activities and the segmented, scaled and weighted spectral data of the training set of compounds using computer implemented statistical pattern recognition, the spectral data-activity relationship comprising a set of canonical variate factors; and using the spectral data-activity relationship to predict the biological activity of the test compound from the segmented spectral data for the test compound.

51. A method for predicting a biological property of a test compound, comprising:

providing spectral data for a training set of compounds having known biological activities, wherein the spectral data for the training set of compounds comprises $^{13}C$ NMR data;

providing spectral data for the test compound, wherein the spectral data for the training set of compounds comprises $^{13}C$ NMR data;

segmenting the spectral data for the test compound into bins to provided segmented spectral data for the test compound, wherein segmenting into bins comprises segmenting the $^{13}C$ NMR data into bins having a width from 0.5 ppm to 5.0 ppm;

segmenting the spectral data for the training set of compounds into bins, wherein segmenting into bins comprises segmenting the $^{13}C$ NMR data into bins having a width from 0.5 ppm to 5.0 ppm;

scaling the spectral data of the training set of compounds in the bins;

weighting the spectral data of the training set of compounds in the bins;

establishing a spectral data-activity relationship between the known biological activities and the segmented, scaled and weighted spectral data of the training set of compounds using computer implemented statistical pattern recognition; and using the spectral data-activity relationship to predict the biological activity of the test compound from the segmented spectral data for the test compound.

52. A computer implemented method for predicting the biological activity of a test compound, comprising:

receiving as input spectral data for a test compound;

receiving as input training set data, the training data comprising spectral data and biological activities of a training set of compounds;

segmenting the spectral data of the training set into bins;

autoscaling the spectral data of the training set;

Fisher-weighting the spectral data of the training set;

using a pattern recognition method to establish a spectral data-activity relationship that classifies compounds of the training set into two or more endpoint classes from the segmented, autoscaled and Fisher-weighted spectral data of the training set and the biological activities of the training set;

segmenting the spectral data for the test compound into bins to provide segmented spectral data for the test compound; and using the spectral data-activity relationship to predict the test compound's endpoint class from the segmented spectral data for the test compound.

53. The computer implemented method of claim 52, wherein the spectral data-activity relationship comprises canonical variate factors for the bins.

54. The computer implemented method of claim 52, wherein the spectral data of the test compound and the spectral data of the training set of compounds comprise spectral data selected from the group consisting of nuclear magnetic resonance data, mass spectral data, infrared data, ultraviolet-visible data, fluorescence data, phosphorescence data, and composites thereof.

55. The computer implemented method of claim 54, wherein the spectral data comprises $^1H$, $^{13}C$, $^{15}N$, 17O, $^{19}F$, $^{31}P$ or $^{35}S$ NMR data.

56. The method of claim 55, wherein the spectral data is calculated.

57. The computer implemented method of claim 52, wherein the spectral data of the test compound and the spectral data of the training set of compounds comprise $^{13}C$ NMR data and segmenting into bins comprises dividing the $^{13}C$ NMR data into sub-spectral units having a width from 0.5 ppm to 5.0 ppm.

58. The computer implemented method of claim 57, wherein the $^{13}C$ NMR data comprises calculated $^{13}C$ NMR data.

59. A computer readable medium having stored thereon computer-executable instructions for performing the method of claim 52.

60. The method of claim 52 further comprising testing the spectral data-activity relationship with a validation set of data.

61. The method of claim 52 further comprising leave-one-out cross-validating the spectral data-activity relationship.

62. The method of claim 52, wherein the pattern recognition method is a statistical pattern recognition method.

63. A computer-implemented method for predicting a biological activity of a test compound, comprising:

obtaining spectral data for the test compound;

segmenting the spectral data for the test compound into segmented spectral data for the test compound; and predicting the biological activity of the test compound from the segmented spectral data for the test compound using a spectral data-activity relationship established between segmented, scaled and weighted spectral data and known biological activities for a training set of compounds, wherein the segmented, scaled and weighted spectral data for the training set of compounds is weighted to more heavily weight bins that are associated with the biological activity.

64. The method of claim 63, wherein the spectral data for the test compound and the segmented, scaled and weighted spectral data for the training set of compounds comprise spectral data selected from the group consisting of nuclear magnetic resonance data, mass spectral data, infrared data, ultraviolet-visible data, fluorescence data, phosphorescence data, and composites thereof.

65. The method of claim 64, wherein the spectral data for the test compound and the segmented, scaled and weighted spectral data of the training set of compounds comprise calculated spectral data.

66. The method of claim 65, wherein the calculated spectral data comprises calculated nuclear magnetic resonance data.

67. The method of claim 66, wherein the calculated nuclear magnetic resonance spectral data comprises calculated $^1H$, $^{13}C$, $^{15}N$, $^{17}O$, $^{19}F$, $^{31}P$ or $^{35}S$ nuclear magnetic resonance data.

68. The method of claim 66, wherein the calculated nuclear magnetic resonance data comprises calculated $^{13}$C NMR data.

69. The method of claim 63, wherein the segmented spectral data for the test compound and the segmented, scaled and weighted spectral data for the training set of compounds comprise $^{13}$C NMR data divided into sub-spectral units having a width from 0.5 ppm to 5.0 ppm.

70. The method of claim 63, wherein the segmented, scaled and weighted spectral data for the training set of compounds comprises segmented, auto-scaled and weighted data.

71. The method of claim 70, wherein the segmented scaled and weighed data for the training set of compounds comprises segmented, auto-scaled and Fisher-weighted data for the training set of compounds.

72. The method of claim 63, wherein the spectral data-activity relationship comprises canonical variate factors.

73. A computer-implemented method for predicting a biological activity of a test compound, comprising:

obtaining spectral data for the test compound;

segmenting the spectral data for the test compound into segmented spectral data for the test compound; and predicting the biological activity of the test compound from the segmented spectral data for the test compound using a spectral data-activity relationship established between segmented, auto-scaled and Fisher-weighted spectral data and biological activities of a training set of compounds.

74. The method of claim 73, wherein the spectral data of the test compound and the segmented, auto-scaled and Fisher-weighted spectral data for the training set of compounds comprise $^{13}$C NMR data.

* * * * *